United States Patent
Sano

(10) Patent No.: US 7,825,375 B2
(45) Date of Patent: Nov. 2, 2010

(54) MICROCHIP, METHOD FOR USING SUCH MICROCHIP AND MASS SPECTROMETRY SYSTEM

(75) Inventor: Toru Sano, Tokyo (JP)

(73) Assignee: NEC Corporation, Tokyo (JP)

( * ) Notice: Subject to any disclaimer, the term of this patent is extended or adjusted under 35 U.S.C. 154(b) by 364 days.

(21) Appl. No.: 12/092,357

(22) PCT Filed: Nov. 9, 2006

(86) PCT No.: PCT/JP2006/322395

§ 371 (c)(1),
(2), (4) Date: May 1, 2008

(87) PCT Pub. No.: WO2007/055293

PCT Pub. Date: May 18, 2007

(65) Prior Publication Data

US 2009/0266980 A1      Oct. 29, 2009

(30) Foreign Application Priority Data

Nov. 14, 2005   (JP)   .............................. 2005-328765

(51) Int. Cl.
*H01J 49/00* (2006.01)
(52) U.S. Cl. ...................... 250/288; 250/281; 250/282; 250/423 R; 250/424; 250/425; 250/492.1; 250/492.2
(58) Field of Classification Search .................. 250/281, 250/282, 288, 423 R, 424, 425, 492.1, 492.2
See application file for complete search history.

(56) References Cited

FOREIGN PATENT DOCUMENTS

| JP | 2004533606 A1 | 11/2004 |
|----|---------------|---------|
| JP | 2005515402 A2 | 5/2005  |
| JP | 2005517954 A1 | 6/2005  |
| WO | 2004081555 A1 | 9/2004  |

OTHER PUBLICATIONS

Machiko Fujita et al., "Chip to Shitsuryo Bunsekikei o Mochiita Tanpakushitsu no Kosoku-Kobunkaino 2 Jigen Mapping", Dai 52 Kai Oyo Butsurigaku Kankei Rengo Koenkai Koen Yokoshu separate vol. 3, Mar. 29, 2005, p. 1458.

E. Gelpi, Journal of Mass Spectrometry, 37, 241-253.

M.L. Mok and additional four persons, The Analyst, 2004, 129, 109-110.

*Primary Examiner*—Jack I Berman
*Assistant Examiner*—Hanway Chang
(74) *Attorney, Agent, or Firm*—Sughrue Mion, PLLC

(57) ABSTRACT

A microchip 100 is employed as target board of mass spectrometry. The microchip 100 includes a substrate 120, a plurality of sample-distributing sections, provided in the substrate 120 and contains samples that serve as a target of a mass spectrometry distributed therein, and a reference material-supplying channel provided in the substrate 120 and capable of being supplied with a reference material in the mass spectrometry. The plurality of sample-distributing sections are provided in the lateral side of the fine channel 102 for distributing the reference material along the fine channel 102 for distributing the reference material.

15 Claims, 12 Drawing Sheets

FIG. 6
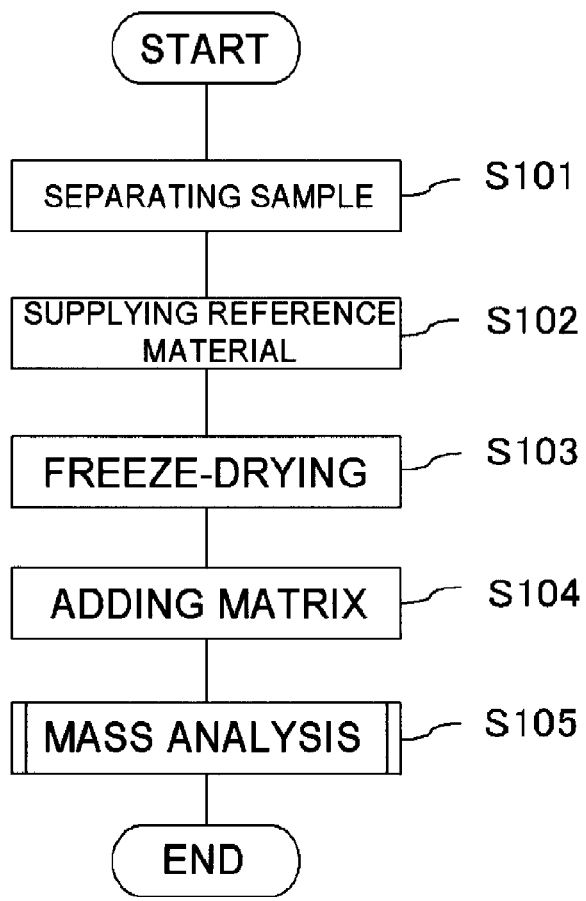
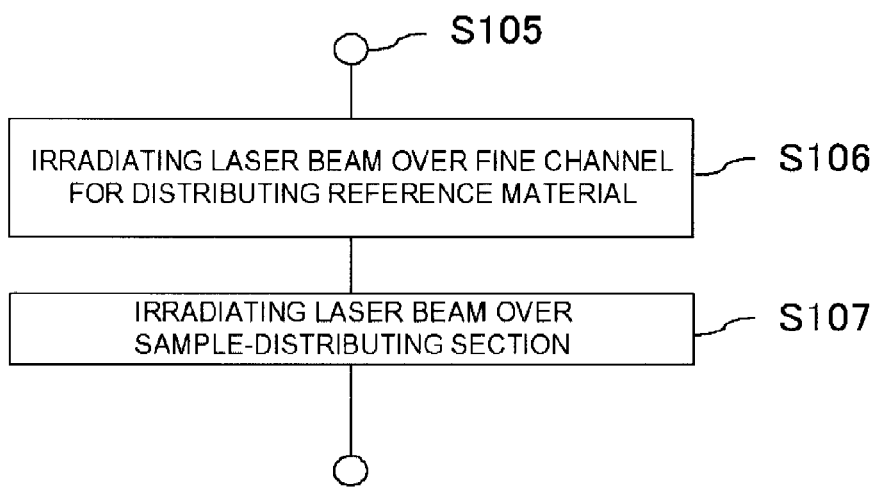

MICROCHIP, METHOD FOR USING SUCH MICROCHIP AND MASS SPECTROMETRY SYSTEM

TECHNICAL FIELD

The present invention relates to a microchip and a method for using thereof, and a mass spectrometry system.

BACKGROUND ART

In recent years, developments of techniques for analyzing solution samples employing microchips have been progressed. In particular, analyses, in which a plurality of constituents in a solution are separated by employing micro passages provided in the microchip and then each of the constituents are detected via various types of detecting techniques, are implemented. A typical exemplary implementation for employing a mass spectrometer as a detecting technique includes a process for analyzing peptide mixtures or the like with a mass spectrometer employing an electro-ion spray ionization after the peptide mixtures or the like are separated via a liquid chromatography (Non-Patent Literature 1).

When a mass spectrometer is employed as a detecting technique, a precision measurement is achieved by measuring a reference material having a known weight prior to measuring samples and then conducting a calibration of the apparatus. In such case, in an electro-ionspray process, a calibration is first carried out by employing the reference material, and then measurements of samples for mass spectrometry are conducted. Since a position of an exhaust-nozzle for an ionized sample is fixed in the electro-ionspray process, once a calibration is achieved, and then theoretically, the measured values do not so greatly deviate when the measurements of samples are sequentially conducted without changing the condition.

On the other hand, another typical ionization process may be a mass spectrometry technique employing a matrix assisted laser desorption/ionization (MALDI) process. The MALDI process is one of processes, in which samples having relatively larger molecular weight such as proteins and the like can be ionized without decomposing thereof.

In a MALDI process, a target plate of several centimeters-square is ordinarily employed, as shown in FIG. 12. A target plate 210 as show in FIG. 12 is, for example, several centimeters-square, and is provided with a plurality of shallow wells 255.

A sample is dropped in the well 255, and further, a matrix serving as an ionization accelerator is dropped therein to prepare a sample for mass spectrometry. Then, the sample for mass spectrometry on a target plate is transferred to a laser spot position by employing an electric stage to conduct a mass analysis.

[Non-Patent Literature 1]

E. Gelpi, Journal of Mass Spectrometry, 37, 241-253.

[Non-Patent Literature 2]

M. L. Mok and additional four persons, The Analyst, 2004, 129, 109-110.

DISCLOSURE OF THE INVENTION

However, when a target plate 210 shown in FIG. 12 is employed for a MALDI time-of-flight (MALDI-TOF) mass spectrometry, a warpage or a non-uniformity in thickness due to a larger dimension of the target plate may induce a concern of causing an error in the mass analysis according to positions in the sample.

In this case, a possible approach for correcting the measurement error may be to arrange wells 256 containing no sample with an appropriate interval, without putting samples for mass spectrometry in all wells 255 of the target plate 210. Then, a reference material for mass calibration is prepared by a method similar to that for the sample for mass spectrometry, and is distributed to the wells 256 that are arranged with an appropriate interval. In the measurement, the wells 256 for the mass calibration are employed to conduct a calibration of the apparatus. Thereafter, the sample for mass spectrometry in the wells 255 that are located in a smaller region near thereof is measured.

It is considered that a precision measurement of mass for all samples for mass spectrometry can be achieved by repetition of such operation. However, when such method is employed, it is necessary to dispose the reference material in a plurality of locations. Thus, a procedure for disposing reference material is onerous.

Alternatively, a possible approach of combining the separated sample by the microchip with the MALDI process may be a configuration that provides wells on the microchip as shown in FIG. 12. Another possible approach may be that the sample is separated on the microchip and the microchip itself is employed as a target of the MALDI-TOF mass spectrometer. A conventional technology described in the Non-patent literature 2 may be for the latter approach.

However, when the conventional microchip is to be directly adopted for the target plate of a MALDI-TOF mass spectrometer, the calibration of the mass in the mass spectrometry is onerous in terms of the following points, according to the investigations of the present inventor.

First, when a plurality of wells are provided on a microchip and are presented in an analyzing process via a spotting of a sample for mass spectrometry similarly as in the conventional target plate, it is necessary to individually spot the reference material one well by one well after an optimum arrangement of the reference material is considered, similarly as in the case of the above described target plate. Thus, the spotting operation of the reference material is onerous.

Secondly, when a mass spectrometry is conducted after a separating operation is conducted in channels in a microchip as described in the Non-patent literature 2, the arrangement of the reference material is onerous. The reason is that the sample for mass spectrometry after the separation is continuously and extensively distributed in the channel, instead of being distributed spot by spot, and that the conventional microchip is not capable of effectively distributing the reference material for the sample for mass spectrometry in all positions. The reason is that, when the method of distributing the reference material spot by spot as in the conventional technique is employed, an optimum distribution should be considered and then larger quantities of spotting for the reference material should be conducted in extreme vicinity of the channel.

The present invention is made on the basis of the above-described circumstances, and is directed to provide a simple and easy technology of conducting a precise calibration that employs the reference material in the mass spectrometry employing a microchip as a target board.

According to one aspect of the present invention, there is provided a microchip, which is capable of being employed as a target board of a mass spectrometry, comprising: a substrate; a plurality of sample-distributing sections, provided in the substrate and containing a sample for mass spectrometry distributed therein; and a reference material-supplying channel, provided in the substrate and being supplied with the reference material for the aforementioned mass spectrometry, wherein the plurality of sample-distributing sections are provided in the lateral side of the reference material-supplying channel along the reference material-supplying channel.

Since the microchip of the present invention is directly employed as a target board, as described above in the "BACKGROUND ART", a precise calibration is required in positions where the samples are arranged or in other words in the sample-distributing sections. Moreover, since a plurality of sample-distributing sections are provided in the single microchip, calibrations are required for the respective sample-distributing sections.

To solve the problem, the microchip of the present invention is provided with the reference material-supplying channels in the substrate. Having this configuration, the reference material can be supplied into the entire reference material-supplying channels in a single supply operation. Then, a plurality of sample-distributing sections are provided in the lateral side of the reference material-supplying channels along thereof. Thus, a use of a single reference material-supplying channel can achieve each of the calibrations for a plurality of sample-distributing sections. Moreover, a single supply of the reference material described above is enough for the measurements of a plurality of sample-distributing sections.

Moreover, in the microchip of the present invention, a plurality of sample-distributing sections are provided in the lateral side of the reference material-supplying channels. Thus, when the microchip of the present invention is employed as a target board of a mass spectrometry, a minimum positional move between the sample-distributing section and the reference material introducing unit is enough for acquisitions of the calibration data and the measurement data of the samples.

As described above, by employing the microchip of the present invention as the target board of the mass spectrometry, simple and precise calibrations can be achieved. Thus, simple and precise analyses can be achieved for the respective samples arranged in plurality of sample-distributing sections.

In the microchip of the present invention, the plurality of sample-distributing sections may be provided in the sample-distributing channel provided in the substrate, and the sample-distributing channel may be provided along the reference material-supplying channel, and the reference material-supplying channel and the sample-distributing channel may be provided in the substrate to form trench-like arrangement, and the configuration thereof may be provided so that constituents in the sample are separated in the sample-distributing channels.

Since a plurality of sample-distributing sections are provided in the sample-supplying channel in such configuration, the whole sample-supplying channel is configured to be capable of functioning as a sample-distributing section. The configuration is provided so that the constituents in the sample are separated within the sample-supplying channel, and at least a portion of the sample-supplying channel functions as a sample-separating region. The constituents in the sample are separated in the sample-supplying channel to be distributed in a plurality of locations in the sample-supplying channel, or in other words in a plurality of sample-distributing sections. Geometries of the plurality of sample-distributing sections may be, for example, band-shaped or spot-shaped.

Moreover, since both of the sample-supplying channel and the reference material-supplying channel are provided to be trench-shaped in such configuration, the configuration is capable of being stably manufactured with higher accuracy by a micro-fabrication.

In the present invention, the configuration may be provided so that an isoelectric focusing of the constituents in the sample is achieved within the sample-supplying channel. More specifically, the microchip of the present invention may also be configured that the sample-distributing channel includes an isoelectric focusing region, in which a pH gradient is created, and further comprising a pair of electrode that applies an electric field to the isoelectric focusing region and a sample-supplying unit that supplies the sample into the isoelectric focusing region. Having this configuration, the isoelectric focusing and the mass spectrometry may be sequentially conducted. Thus, if the sample is in very small amount in cases of living body sample or the like, no loss of the sample is caused, and thus the analysis can be surely carried out.

The microchip of the present invention may also be configured that the sample-distributing channel is disposed along a direction of an elongation of the reference material-supplying channel in substantially parallel therewith. Having such configuration, the configuration that provides further improved manufacturing stability can be achieved. Moreover, the separation of the constituent in the sample can be further stably conducted. Moreover, since it is sufficient to move the position of the analysis on the microchip on a straight line when the microchip is employed as a target board of a mass spectrometry, and thus the analysis operation can be more stably conducted.

The microchip of the present invention may also be configured that planar shapes of the reference material-supplying channel and the sample-distributing channel are zigzag-shaped. Having such configuration, an increased channel length of the sample-supplying channel can be utilized, so that an improved separability is achieved. Further, more sample-distributing sections can be provided in a single sample-supplying channel, so that analyses of larger number of constituents can be conducted on a single piece of the microchip.

The microchip of the present invention may also be configured that the reference material-supplying channel is provided in the substrate to form a trench-shape, wherein the plurality of sample-distributing sections are a plurality of pores discretely provided in the substrate, and wherein the plurality of pores are provided in a lateral side of the reference material-supplying channel along the reference material-supplying channel.

In such configuration, a common reference material-supplying channel can be employed for a plurality of pores. Since the standard samples can be disposed over the entire the reference material-supplying channel by a single supply operation, simple and easy operation of supplying the reference material can be utilized.

Further, since a plurality of pores are provided in the lateral side of the reference material-supplying channels along the reference material-supplying channels in such configuration, the calibrations can be conducted for the respective pores by employing regions in the reference material-supplying channel near thereof. Thus, when the measurements are conducted for a plurality of pores, an improved calibration accuracy can be achieved for each of the pores.

The microchip of the present invention may also be configured that a planer shape of the reference material-supplying channel is zigzag-shaped. Having such configuration, still more pores can be disposed in the lateral side of the reference material-supplying channel, so that possible number of the samples to be measured by using a single piece of the microchip can be increased. Further, even in the case of the configuration that the pores are two-dimensionally arranged in the surface of the substrate, the respective pores can be surely arranged in the lateral side of the reference material-supplying channel.

The microchip of the present invention may also be configured that a distance between the sample-distributing section and the reference material-supplying channel in the substrate surface is equal to or larger than 0.5 mm and equal to or smaller than 10 mm. By selecting the distance between the sample-distributing section and the reference material-supplying channel to be equal to or larger than 0.5 mm, a mixing of the substances in the sample-distributing section and the substances in the reference material-supplying channel can be further effectively inhibited. On the other hand, by selecting the distance between the sample-distributing section and the reference material-supplying channel to be equal to or smaller than 10 mm, an error caused by a misalignment of the sample-distributing section with the reference material-supplying channel can be further reduced. Thus, the calibration in the mass spectrometry can be conducted with further improved certainty. In addition to above, the distance between the sample-distributing section and the reference material-supplying channel may indicate, for example, the shortest distance between an end section of the sample-distributing section and an end section of the reference material-supplying channel.

The microchip of the present invention may also be configured that a material of the substrate is silicone resin, silicon or glass.

Having such configuration, the configuration is capable of stably manufacturing the regions that will be the reference material-supplying channel and a sample-distributing section with higher accuracy by employing a microfabrication process. Typical silicone resin may be, more specifically, poly dimethylsiloxane.

The microchip of the present invention may also be configured that a plurality of columnar member are provided in the reference material-supplying channel. The formation of such fine structure in the channel provides the configuration that a liquid containing the reference material further easily flows into the reference material-supplying channel.

The microchip of the present invention may also be configured that a hydrophilic treatment is conducted for a surface of the reference material-supplying channel. Once the hydrophilic treatment is conducted for the surface of the channel, a liquid containing the reference material can be supplied into the reference material-supplying channel with further certainty, even if the channel is fine.

The microchip of the present invention may also be configured that, in a surface for forming the reference material-supplying channel in the substrate, a water repellent treatment is conducted for at least a vicinity of a region for forming the reference material-supplying channel. This can avoid a mixing of the liquid in the reference material-supplying channel with the sample on the sample-distributing section, so that a contamination of the sample can be further effectively inhibited.

According to another aspect of the present invention, there is provided a method of employing the microchip of the present invention as described above as a target board of mass spectrometry, comprising: disposing a sample in the sample-distributing section, the sample serving as a target of a mass spectrometry; supplying a reference material for the mass spectrometry in the reference material-supplying channel; and conducting a laser desorption/ionization (LDI) time of flight mass spectrometry (TOFMS) of the sample, wherein the aforementioned conducting the LDI-TOFMS includes: irradiating a laser beam over a predetermined region of the reference material-supplying channel; and irradiating a laser beam over the sample-distributing section located near the predetermined region among the plurality of sample-distributing sections.

In such method, the microchip is employed as a target board of a mass spectrometry, and the operation of conducting the laser desorption/ionization mass spectrometry includes the operation of irradiating a laser beam over the sample-distributing section.

Thus, it is required to conduct a calibration for the position where a laser beam is irradiated, or in other words for the sample-distributing section. Further, since the operation of conducting the flight time mass spectrometry is included, a presence of an irregularity or a distortion in the microchip adversely affects a flight time, easily causing an error in the measured value. Thus, calibrations are required for the respective plurality of sample-distributing sections.

To solve the problem, in the present invention, the microchip having the above-described configuration is employed, and a predetermined region of the reference material-supplying channel is irradiated with a laser beam, and then the sample-distributing section located near the predetermined region is irradiated with a laser beam among the plurality of sample-distributing sections. Having such configuration, simple and assured calibrations can be conducted for a plurality of sample-distributing sections on the microchip.

According to further aspect of the present invention, there is provided a mass spectrometry system, comprising: a microchip of the present invention as described above; an optical irradiation unit, which is capable of irradiating a laser beam over a predetermined region of the reference material-supplying channel and is capable of irradiating a laser beam over the sample-distributing section near the predetermined region among the plurality of sample-distributing sections; a data acquisition unit, which is capable of analyzing ion of the reference material created by the irradiation over the reference material-supplying channel to acquire a mass spectrometry data of the reference material and is also capable of analyzing ion of the sample created by the irradiation over the sample-distributing section near the predetermined region to acquire a mass spectrometry data of the sample; and an analyzing unit, which is capable of acquiring calibration data for mass spectrometry of the sample based on the mass spectrometry data of the reference material to analyze mass spectrometry data of the sample based on the calibration data.

In the mass spectrometry system of the present invention, the optical irradiation unit is configured to irradiate beams over both of the reference material-supplying channel and the sample-distributing section disposed near thereof. Thus, the calibration of the mass spectrometry data of the sample in the sample-distributing section can be ensured by employing the microchip as a target board of the mass spectrometry and by employing calibration data.

The mass spectrometry system of the present invention may also be configured that a distance between the aforementioned sample-distributing section and the aforementioned reference material-supplying channel in the surface of the substrate is larger than a spot diameter of the aforementioned laser beam. Having such configuration, in the measurements of the reference material and the samples, the separation of both of mass spectrum signals can be more definitely achieved.

As described above, according to the present invention, a simple and easy technology of conducting a precise calibration that employs the reference material is provided in the mass spectrometry employing a microchip as a target board.

BRIEF DESCRIPTION OF THE DRAWINGS

The above objects and other objects, advantages and features will be more apparent from the following description of preferred embodiments taken in conjunction with the following accompanying drawings.

[FIG. 6] It is a flow chart of an analysis procedure in an embodiment.

BEST MODE FOR CARRYING OUT THE INVENTION

Exemplary implementations according to the present invention will be described as follows in reference to the annexed figures. In all figures, an identical numeral is assigned to an element commonly appeared in the figures, and the detailed description thereof will not be repeated.

FIRST EMBODIMENT

Figure 1:
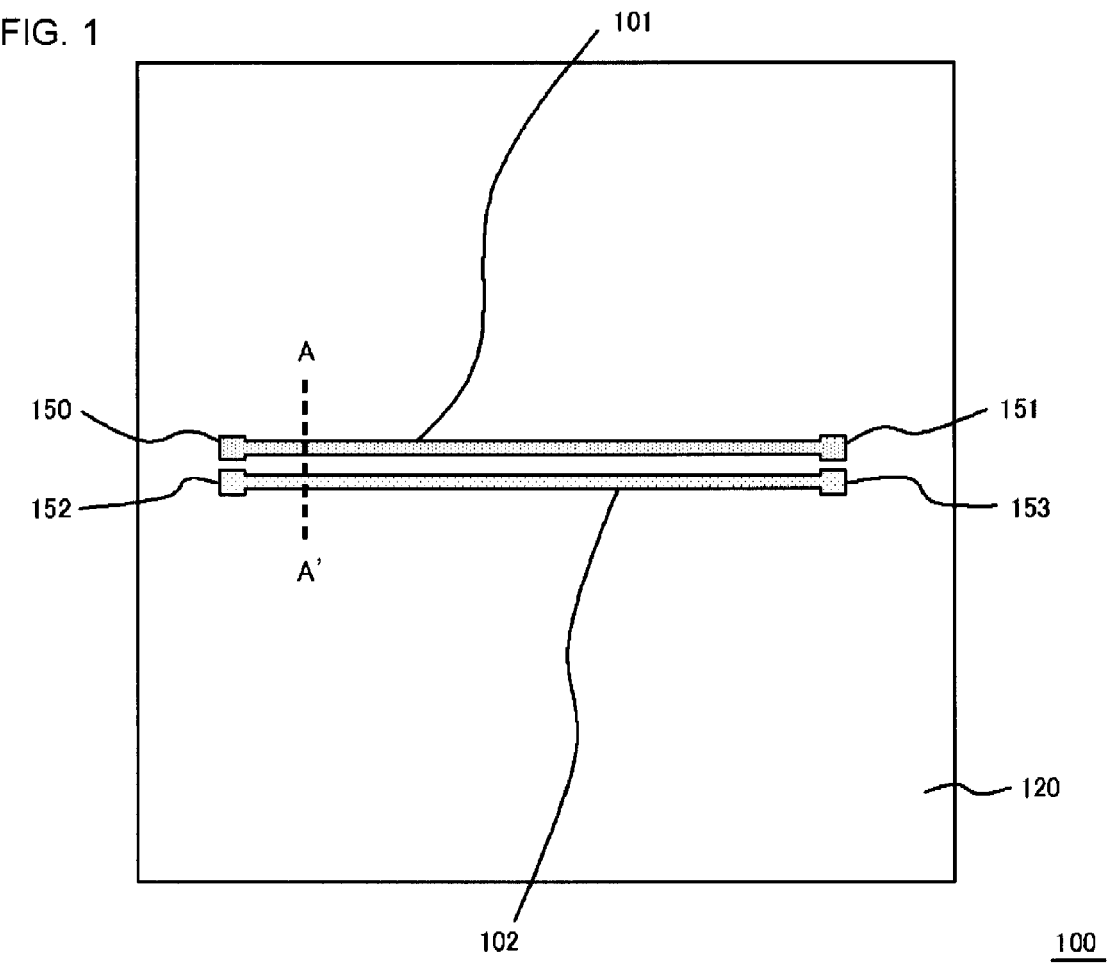
[FIG. 1] It is a plan view, illustrating a configuration of a microchip in an embodiment.

FIG. 1 is a plan view, illustrating a configuration of a microchip in the present embodiment. A microchip 100 shown in FIG. 1 is a microchip, which is capable being employed as a target board of a mass spectrometry, and includes a substrate 120, a plurality of sample-distributing sections, provided in the substrate 120 and contains samples that serve as a target of a mass spectrometry distributed therein, and a reference material-supplying channel (fine channel 102 for distributing reference material), provided in the substrate 120 and capable of being supplied with a reference material in the mass spectrometry. The plurality of sample-distributing sections are provided in vicinity of the fine channel 102 for distributing the reference material. Further, the plurality of sample-distributing sections are provided in the lateral side of the fine channel 102 for distributing the reference material along the fine channel 102 for distributing the reference material. In the microchip 100, a plurality of sample-distributing sections are provided in the sample-supplying channel (channel 101 for separation) provided in substrate 120.

The channel 101 for separation and the fine channel 102 for distributing the reference material are channels provided in the substrate 120 to be trench-shaped. The depth of channel for separation 101 may be selected as being substantially same as the depth of the fine channel 102 for distributing the reference material. Having such configuration, the calibration in the mass spectrometry can be conducted with further improved certainty.

The fine channel 102 for distributing the reference material is in communication with a liquid receiver 152 and a liquid receiver 153 in both ends, respectively. A liquid containing the reference material in the mass spectrometry is supplied to the fine channel 102 for distributing the reference material. A hydrophilic treatment may be conducted for a surface of the fine channel 102 for distributing the reference material. Once the hydrophilic treatment is conducted for the surface of the channel, the reference material can be supplied into the fine channel 102 for distributing the reference material with further certainty, even if the channel is fine.

The channel 101 for separation is provided along the fine channel 102 for distributing the reference material, and is provided in vicinity of and in parallel with the fine channel 102 for distributing the reference material.

In the microchip 100, the channel 101 for separation is disposed in substantially parallel with an elongating direction of the fine channel 102 for distributing the reference material. This allows providing a substantially constant distance between the channel 101 for separation and the fine channel 102 for distributing the reference material, so that a variation in the accuracy in the calibration for a plurality of constituents separately disposed in the channel 101 for separation can be reduced. Further, a simple and easy moving of the stage in the mass spectrometry can be achieved.

The channel 101 for separation is a trench-shaped channel provided in the substrate 120, and is in communication with a liquid receiver 150 and a liquid receiver 151 in both ends, respectively. A liquid containing the sample of the mass spectrometry target is supplied to the liquid receiver 151 or the liquid receiver 152. At least a portion of the channel 101 for separation serves as a sample-separating region, and is configured that the constituents in the sample are separated in the channel 101 for separation. The constituents in the sample supplied to the channel 101 for separation are separated in the channel 101 for separation by a certain process to be disposed in a plurality of locations in the channel 101 for separation, or in other words in a plurality of sample-distributing sections. The constituents in the sample are separated in a pattern of, for example, a plurality of band-shape or a plurality of spot-shape, and are discretely disposed in the channel 101 for separation.

In the present embodiment and the following embodiments, descriptions will be made in reference to exemplary implementations, in which the constituents in the sample are separated in the channel 101 for separation by an isoelectric focusing.

The channel 101 for separation includes an isoelectric focusing region, in which a pH gradient is created, and further includes a pair of electrodes (not shown) that are capable of applying an electric field to the isoelectric focusing region, and a sample-supplying units (liquid receiver 150, liquid receiver 151) that introduce the sample into the isoelectric focusing region. When an electric field is applied between the liquid receiver 150 and the liquid receiver 151, the whole channel 101 for separation can be utilized as the isoelectric focusing region.

In addition to above, though it is not shown in FIG. 1, electrode-distributing sections may be provided in the liquid receiver 150 and the liquid receiver 151 that are in communication with the channel 101 for separation. In such case, a pair of electrodes may be, for example, bar-like metallic members, which are inserted in the liquid receiver 150 and the liquid receiver 151. Further, inner walls of the liquid receiver 150 and the liquid receiver 151 may be covered with metallic films to provide the electrodes. Further, since the fine channel 102 for distributing the reference material is a channel for disposing the reference material and does not serve for separating the sample, no electrode-distributing section distribution is provided in the liquid receiver 152 and the liquid receiver 153 that are in communication with the fine channel 102 for distributing the reference material.

A distance between the channel 101 for separation and the fine channel 102 for distributing the reference material in the surface of the substrate may be preferably larger than a spot diameter of a laser beam irradiated over the substrate 120, in view of definitely separating spectroscopic signal of the reference material and the sample in the measurement of the mass spectrometry, and may be, for example, equal to or larger than 0.5 mm, and more preferably equal to or larger than 2 mm. This can provide further definite inhibition of a contamination by one of a liquid in the fine channel 102 for distributing the reference material and a liquid in the channel 101 for separation to the other.

Further, a distance between the channel 101 for separation and the fine channel 102 for distributing the reference material in the surface of the substrate may be, for example, equal to or smaller than 10 mm, and preferably equal to or smaller than 5 mm, in view of further effectively reducing a misalignment of the channel 101 for separation with the fine channel 102 for distributing the reference material.

A material of the substrate 120 may typically be glass such as quartz. Other materials may also be employed. Other materials for the substrate 120 include, for example, silicone resins such as poly dimethylsiloxane (PDMS), and silicon. By employing such materials, the fine channel 102 for distributing the reference material and the channel 101 for separation can be stably manufactured in the substrate 120 with higher accuracy by employing a microfabrication process. In a surface for forming the fine channel 102 for distributing the reference material in the substrate 120, a water repellent treatment may be conducted for at least a vicinity of a region for forming the fine channel 102 for distributing the reference material. This can prevent a liquid in the fine channel 102 for distributing the reference material from overflowing from the fine channel 102 for distributing the reference material over the upper surface of the substrate 120. Thus, a mixing of materials in the fine channel 102 for distributing the reference material with the sample in the channel 101 for separation can be avoided, such that a contamination of the sample can be further effectively inhibited.

Next, a method for manufacturing the microchip 100 will be described. The microchip 100 is manufactured by forming a structure including the channel 101 for separation and the fine channel 102 for distributing the reference material by employing a technology of a known dry etching or wet etching over the substrate 120 composed of a certain material.

Further, a water repellent treatment may be previously conducted over the regions of the surface of the substrate 120 except the regions where the channel 101 for separation, the fine channel 102 for distributing the reference material and the respective liquid receivers are formed. This configuration can avoid the overflow of the reference material solution from the fine channel 102 for distributing the reference material, which may otherwise cause a mixing with the samples for mass spectrometry that have been arranged in vicinity thereof. Further, the opposite contamination can also be avoided. Thus, a contamination caused by a mixing of the sample in the channel 101 for separation with the sample in the fine channel 102 for distributing the reference material can be avoided. Specific method of the water repellent treatment may include, for example, a method for coating a predetermined region in the surface of the substrate 120 with a water repellent material such as Teflon™ and the like. After the coating, a fine structure of sections where a liquid is contacted thereto, such as the channel 101 for separation, may be manufactured by employing the following method.

More specifically, first of all, an optical mask having a geometry corresponding to that of the channel 101 for separation and the fine channel 102 for distributing the reference material is prepared. Then, an optical resist is applied over the substrate 120 by a spin coating process. Subsequently, the previously prepared mask is employed to expose the optical resist to light through a channel pattern, and then a development process is conducted to prepare a patterned resist. Then, a dry etching or a wet etching process of the substrate 120 are conducted through a mask of the obtained patterned resist to form the channel 101 for separation, the fine channel 102 for distributing the reference material and each of the liquid receivers that communicate therewith.

Then, an ozone ashing process or a coating process is conducted to provide a hydrophilic treatment over the surface of the obtained microchip 100. Since the hydrophilic treatment for the surface of the microchip 100 provides hydrophilicity over the inner wall of the fine channel 102 for distributing the reference material, the resultant configuration allows a solution of the water-soluble reference material to be easily flowed into the fine channel 102 for distributing the reference material. The microchip 100 shown in FIG. 1 is thus obtained by the above-described procedure.

In the microchip 100, the fine channel 102 for distributing the reference material, which extends through the vicinity of all the sample for mass spectrometry contained in respective compartments that are separated to have relatively larger dimension, is provided in the substrate 120 that includes the fine channel 101 for separation, which is capable of having the samples for the mass spectrometry disposed therein. Thus, for all the samples for mass spectrometry, a shorter distance with the reference material for calibration can be maintained. Further, since the fine channel 102 for distributing the reference material is disposed in parallel with the channel 101 for separation in the microchip 100, the distances from the reference material to respective samples for mass spectrometry can be provided to be substantially constant.

Further, in the microchip 100, distances, which are not smaller than the diameter of the laser beam spot of the employed mass spectrometer, are provided between the fine channel 102 for distributing the reference material and the respective samples for mass spectrometry. Thus, in the measurements of the reference material and the respective samples for mass spectrometry, both of the mass spectrum signals can be definitely separated. Further, the distance between the fine channel 102 for distributing the reference material and the sample for mass spectrometry is set to, for example, equal to or shorter than 10 mm, so that a move of a stage in the measurements of the reference material and the respective samples for mass spectrometry can be reduced to a distance of about 10 mm at a maximum. Thus, more efficient mass spectrometry can be achieved.

In addition to above, in the microchip 100 shown in FIG. 1, the upper portions of the channel 101 for separation and the fine channel 102 for distributing the reference material may be coated, and are provided with removable seals.

Figure 4:
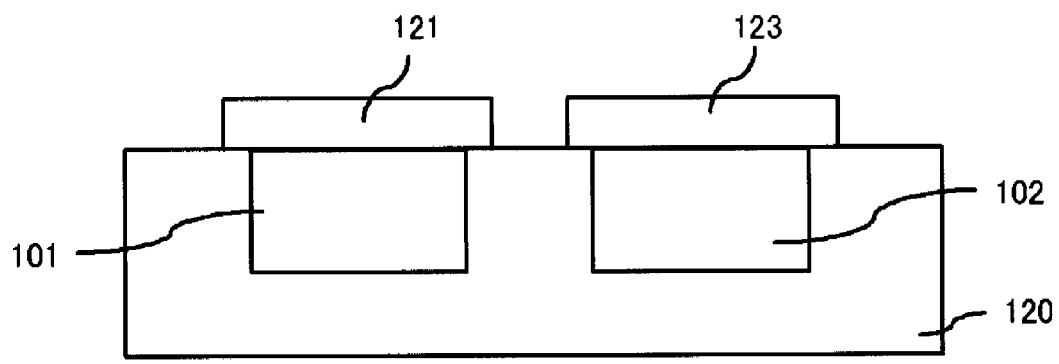
[FIG. 4] It is an A-A' cross-sectional view in FIG. 1.

FIG. 4 is a diagram, illustrating an example for providing seals to the microchip 100. FIG. 4 corresponds to a cross-sectional view of FIG. 1 along line A-A'. In FIG. 4, a first seal 121 and a second seal 123 are provided on the upper portions of the channel 101 for separation and the fine channel 102 for distributing the reference material, respectively. The first seal 121 and the second seal 123 covers an upper of a channel 101 for separation and the fine channel 102 for distributing the reference material respectively. The first seal 121 and the second seal 123 are provided as film-like members, and the planer shapes thereof are, for example, rectangular shapes. Further, one end of the seals may be in a condition of disengagement, without being adhered to the substrate 120. This can provide an easy detachment of the seals from the substrate 120.

Typical material available for the first seal 121 and the second seal 123 may be, for example, silicone resins such as PDMS and the like. An adhesiveness of silicone resin provides a fine coverage over the channels provided in the surface of the substrate 120. Further, a water repellency of silicone resin inhibits a capillary effect caused in the removal of the first seal 121 and the second seal 123, thereby preventing a contamination of the sample or the constituents in the sample in the channels. In addition to above, an improved coverage effect by the adhesiveness of silicone resin may also be achieved by selecting silicone resin for the material of the substrate 120.

By providing the first seal 121 and the second seal 123, the channel 101 for separation and the fine channel 102 for distributing the reference material can be definitely covered, and can also be easily opened as required. Thus, contamination of the channel 101 for separation and the fine channel 102 for distributing the reference material during a separating operation in the channel 101 for separation can be more effectively inhibited. Then, after the separation, a separation pattern in the channel 101 for separation and the reference material in the fine channel 102 for distributing the reference material are immobilized by freezing or the like, and then the first seal 121 and the second seal 123 are detached from disengaged section of the end to expose the upper portions of the respective channels. Thereafter, when the mass spectrometry is conducted, each of the channels can be directly irradiated with laser beam.

While the seals covering the channel 101 for separation and the fine channel 102 for distributing the reference material are of different members in FIG. 4, a common single seal may alternatively be provided to cover these channels. A use of the common seal requires only a single detachment operation, and thus further simple and easy operation can be provided.

Alternatively, in the microchip 100 shown in FIG. 1, a covering substrate (not shown) that covers the upper portion of the substrate 120 may further be provided. In the covering substrate, through holes may be provided in regions disposed above the liquid receiver 150, the liquid receiver 151, the liquid receiver 152 and the liquid receiver 153. The covering substrate may be detachable from the substrate 120. Alternatively, trench-like through holes may be provided in positions corresponding to portions of the covering substrate above the channel 101 for separation and above the fine channel 102 for distributing the reference material, and the upper portions of the through holes may be covered with the detachable first seal 121 and second seal 123.

While the case of the flat surface of the fine channel 102 for distributing the reference material is illustrated in FIG. 1, fine bumpy structures may alternatively be formed in the surfaces of these channels. More specifically, a plurality of columnar members (pillars) may be formed over the entire fine channel 102 for distributing the reference material via a microfabrication process to provide patterned pillars.

Figure 5:
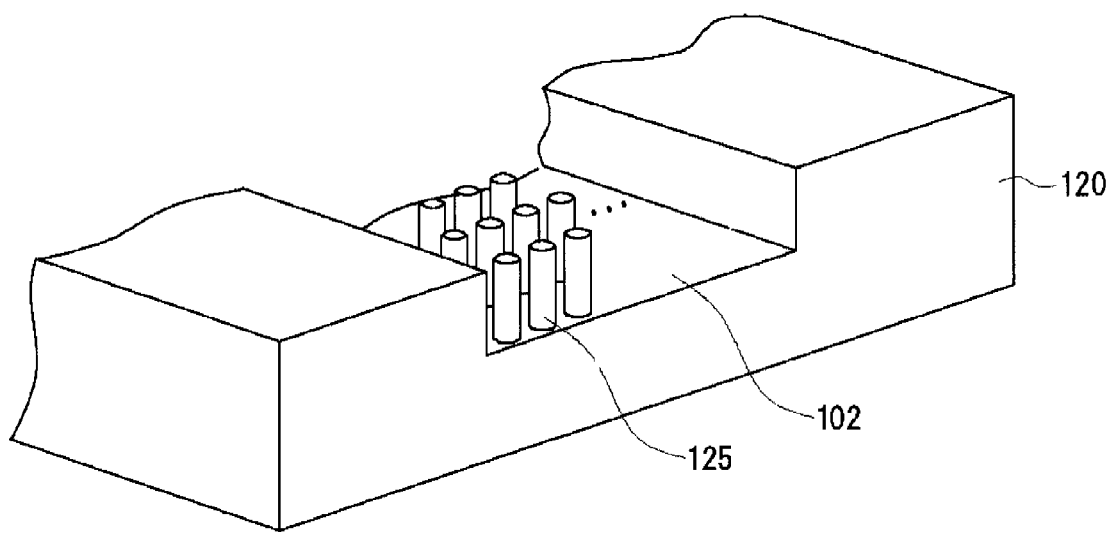
[FIG. 5] It is a perspective view, illustrating a configuration of fine channels for arranging reference material in the microchip in an embodiment.

FIG. 5 is a diagram, illustrating a condition where a plurality of cylindrical pillars are disposed in the fine channel 102 for distributing the reference material. In FIG. 5, a plurality of pillars 125, which protrude from the bottom surface of the fine channel 102 for distributing the reference material toward the inside thereof is regularly arranged. The plurality of pillars 125 may be, for example, distributed to form a lattice pattern. Typical lattice pattern distribution may be, more specifically, a distribution of a diagonal lattice pattern such as hound's-tooth pattern and the like, or a distribution of a tetragonal lattice pattern.

By providing the pillars 125 in the fine channel 102 for distributing the reference material, it can be configured that the reference material is more easily flowed into the fine channel 102 for distributing the reference material, even if the fine channel 102 for distributing the reference material is narrow.

Next, a method for using the microchip 100 will be described. FIG. 6(a) and FIG. 6(b) are flow charts of the mass spectrometry that employs the microchip 100. The microchip 100 is used as a target board of the mass spectrometry. The method includes the following steps as shown in FIG. 6A.

Step 101: a step for disposing target samples of mass spectrometry in sample-distributing sections (plurality of locations in channel 101 for separation);

Step 102: a step for supplying the reference material for mass spectrometry into the fine channel 102 for distributing the reference material; and Step 105: a step for conducting a laser desorption/ionization time of flight mass spectrometry of the sample.

In step 101, the samples are separated in the channel 101 for separations, so that the samples are discretely distributed in plurality of locations in the channel 101 for separation.

Further, the following steps may be further added between step 102 and step 105.

Step 103: a step for freeze-drying liquids in the channel 101 for separation and in the fine channel 102 for distributing the reference material; and Step 104: a step for adding a matrix in the channel 101 for separation and the fine channel 102 for distributing the reference material.

In the following description, an exemplary implementation of conducting a mass spectrometry via a MALDI-TOFMS process in step 105 will be described. First, process steps before the mass spectrometry of step 105 will be described.

First of all, constituents as target substances in the sample for mass spectrometry are separated in the channel 101 for separation of the microchip 100 (S101). More specifically, electrophoresis separation is conducted in the channel 101 for separation by utilizing an appropriate physical or chemical property of, for example size or isoelectric point. In such case, a sample solution for electrophoresis is prepared, and is supplied to the channel 101 for separation, and then electrodes (not shown) are inserted in the liquid receiver 150 and the liquid receiver 151, respectively, and a voltage is applied to the electrode to conduct a separating operation. Alternatively, a separation process of applying a pressure may be employed, instead of the separation process of applying a voltage.

After the separation, the separated samples are dried via a process such as a freeze drying process (S103) to be fixed in discrete positions in the channel 101 for separation. By these procedures, the sample for mass spectrometry such as protein and the like is dry-fixed on the microchip 100. Then, a matrix, which is preferable for mass measurement materials, is added in the channel 101 for separation by employing a certain process such as a spraying process or a dropping process (S104). This allows mixing the mass measurement material with the matrix to create mixed crystal. Having such configuration, MALDI-TOF (time-of-flight) mass spectrometry can be conducted.

Since the channel 101 for separation is provided in the microchip in the present embodiment and second embodiment, the constituents in the sample are separated in the channel 101 for separations and can be presented for mass spectrometry without taking the separated constituent out from the channel 101 for separation.

On the other hand, before drying the liquid in the channel 101 for separation, a liquid prepared by adding and mixing a plurality of materials, mass of which are known, is supplied to the fine channel 102 for distributing the reference material as a reference material for mass calibration (S102). Concerning the plurality of materials, mass of which are known, are, for example, a material having molecular weight corresponding to the constituents in the sample as the measurement object is selected. In such occasion, the reference material is supplied to the liquid receiver 150 or the liquid receiver 151, which are in communication with an end section of the channel 101 for separation. Having such procedure, in the micro channel-like fine channel 102 for distributing the reference material, the reference material flows into such channel by a capillary phenomenon, reaching the liquid receiver formed in the opposite end. This allows the entire fine channel 102 for distributing the reference material to be filled with the reference material by a single supplying operation.

In addition to above, when the reference material is supplied in the fine channel 102 for distributing the reference material, a vacuum tweezers may be brought to be closer to one of the liquid receiver 152 and the liquid receiver 153, which is provided to a side opposite to another side having the liquid receiver employed in supplying the reference material, so that the reference material would be drawn into the fine channel 102 for distributing the reference material. Having this configuration, even if the fine channel 102 for distributing the reference material is microscopic, the reference material can be supplied into the fine channel 102 for distributing the reference material with more certainty. Hereafter, for example, the methods described above may be employed to mix the reference material and matrix, so that the MALDI-TOF mass spectrometry can be conducted.

In addition to above, no separating operation is required for the fine channel 102 for distributing the reference material, unlikely as the case of the channel 101 for separation, and it would be sufficient if the reference material be spread out over the entire area of the fine channel 102 for distributing the reference material. To achieve the condition, a pre-mixed solution prepared by mixing the reference material and a preferable matrix may be prepared in advance, and the pre-mixed solution may be poured into the fine channel 102 for distributing the reference material from the liquid receiver 152 or the liquid receiver 153. In this case, after the solvent is evaporated, a mixed crystal of the matrix and the reference material is created over the entire area of the fine channel 102 for distributing the reference material. Concerning the reference material, it is sufficient to measure the reference mass, and some ununiformity in the concentration may be allowed if it does not adversely affect the measuring accuracy.

Next, a procedure for the mass spectrometry in step 105 will be described. In step 105, the step for conducting a laser desorption/ionization time of flight mass spectrometry further includes the following steps as shown in FIG. 6 (b).

Step 106: a step for irradiating a laser beam over a predetermined region of the fine channel 102 for distributing the reference material; and Step 107: a step for irradiating a laser beam over one or some of plurality of sample-distributing sections, which is or are disposed near the aforementioned predetermined region.

In step 105, the microchip 100 is employed as a target board of MALDI-TOF mass spectrometer, and is directly disposed in a predetermined position of the mass spectrometry apparatus. Then, a laser beam is irradiated for the respective constituents, which are separated and distributed in the different positions in the channel 101 for separation to conduct the flight time mass spectrometry. Thus, if the substrate 120 of the microchip 100 has an irregularity and a distortion, a difference is caused in time-of-flight to cause an error in the measurement results. To solve the problem, a calibration employing the reference material is required for the respective constituents in the channel 101 for separation, or in other words the respective spots.

Figure 7:
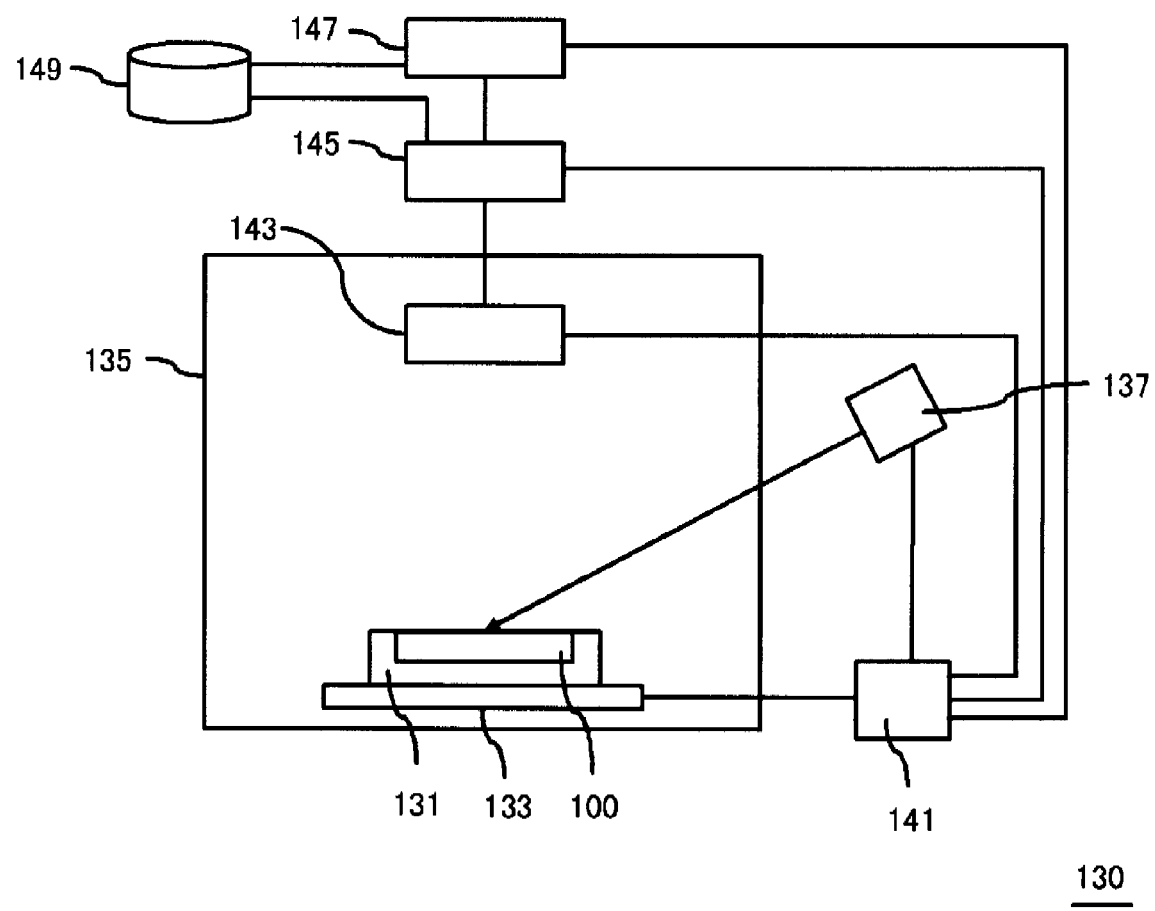
[FIG. 7] It is a diagram, illustrating a configuration of a mass spectrometry system in an embodiment.

FIG. 7 is a diagram, illustrating an example of a configuration of a mass spectrometry system comprising the microchip 100. A mass spectrometry system 130 shown in FIG. 7 comprises: the microchip 100; an optical irradiation unit (laser source 137), which is capable of irradiating a laser beam over a predetermined region of the fine channel 102 for distributing the reference material and is capable of irradiating a laser beam over the sample-distributing section near the aforementioned predetermined region among the plurality of sample-distributing sections of the channel 101 for separation; a data acquisition unit (detecting unit 143), which is capable of analyzing ion of the reference material created by the irradiation over the fine channel 102 for distributing the reference material to acquire a mass spectrometry data of the reference material and is also capable of analyzing ion of the sample created by the irradiation over the sample-distributing section near the predetermined region to acquire a mass spectrometry data of the sample; and an analyzing unit (analyzing unit 145), which is capable of acquiring calibration data for mass spectrometry of the sample based on the mass spectrometry data of the reference material to analyze mass spectrometry data of the sample based on the calibration data. The laser source 137 is capable of irradiating a beam over the surface of the microchip 100. The laser source 137 is configured that an irradiation angle of a beam in an irradiated position is substantially constant to provide an irradiation of a beam over the surface of the microchip 100.

The microchip 100 is mounted to an adaptor 131. The microchip 100 may be designed to be smaller, as compared with a target size of the mass spectrometer. Even in such case, a measurement employing an existing mass spectrometry apparatus can be achieved by preparing the adaptor 131 having an outer shape that is the same as that of a reference target of the mass spectrometer and by mounting such adaptor 131 to the microchip 100. The adaptor 131 having the microchip 100 mounted therein is mounted on a stage 133 in a mass spectrometry chamber 135 to be utilized for mass spectrometry.

The stage 133 is an X-Y stage, and the position thereof is controlled by a controller unit 141 such as a controller computer. By moving the position of the stage 133, the microchip 100 is moved relative to the laser source 137 to allow moving an irradiated position on the surface of the microchip 100 with a laser beam. Further, the stage 133 is also employed as a substrate for forming an electric field in the mass spectrometry.

In the microchip 100, the channel 101 for separation is provided in the lateral side of the fine channel 102 for distributing the reference material along the fine channel 102 for distributing the reference material. Thus, when an acquisition of calibration data and an acquisition of mass spectrometry data of the sample are to be carried out, it is sufficient to at least move relative positions of the microchip 100 and the laser source 137 by moving the stage 133, and thus an effective measurement can be achieved. Further, if the configuration is provided to allow the distance between the channel 101 for separation and the fine channel 102 for distributing the reference material to be larger than a spot diameter of a laser beam in the surface of the substrate of the microchip 100, an improved accuracy of the measurement can be achieved.

In a data storage 149, data of mass and specific charge (m/z) of the relevant material are stored in relation to identifications (ID) of the respective materials employed as the reference material. Further, data on the positional coordinate (N) in an elongating direction of the fine channel 102 for distributing the reference material are stored in the data storage 149. Further, positional information in an elongation direction of the channel 101 for separations are stored in the data storage 149 in relation to the positional coordinate (N) in corresponding fine channel 102 for distributing the reference material. Further, data related to an equation for providing a calibration curve may also be stored in the data storage 149. In addition, measurement data detected by the detecting unit 143 may also be stored in the data storage 149. In such case, either the mass spectrometry data of the reference material or the mass spectrometry data of the sample may be stored in the data storage 149.

The detecting unit 143 provides a detection of a specific charge (m/z) of the constituents of the ionized sample. The analyzing unit 145 acquires a mass spectrometry data detected in the detecting unit 143 and then the data is analyzed. The analyzing unit 145 functions as, more specifically:
(i) a preparation of a calibration curve data by employing the mass spectrometry data of the reference material; and
(ii) an analysis of the mass spectrometry data of the sample by employing the calibration curve data.

In the preparation of the calibration curve by employing the mass spectrometry data of the reference material in the above (i), the analyzing unit 145 creates the calibration curve data on the basis of data of the mass of the respective reference materials stored in the data storage 149 and data of the specific charge of the respective reference material (m/z) obtained by the measurement. In addition, in the analysis of mass spectrometry data of the sample by employing the calibration curve data of the above-described (ii), the analyzing unit 145 acquires data of mass corresponding to data of the specific charges (m/z) of the sample, based on data of the calibration curve obtained in the above-described (i) obtained.

A displaying unit 147 acquires information related to the analysis result in the analyzing unit 145 to display thereof on the screen or on paper.

The controller unit 141 controls operations of the stage 133, the laser source 137, the detecting unit 143, the analyzing unit 145 and the displaying unit 147.

Figure 8:
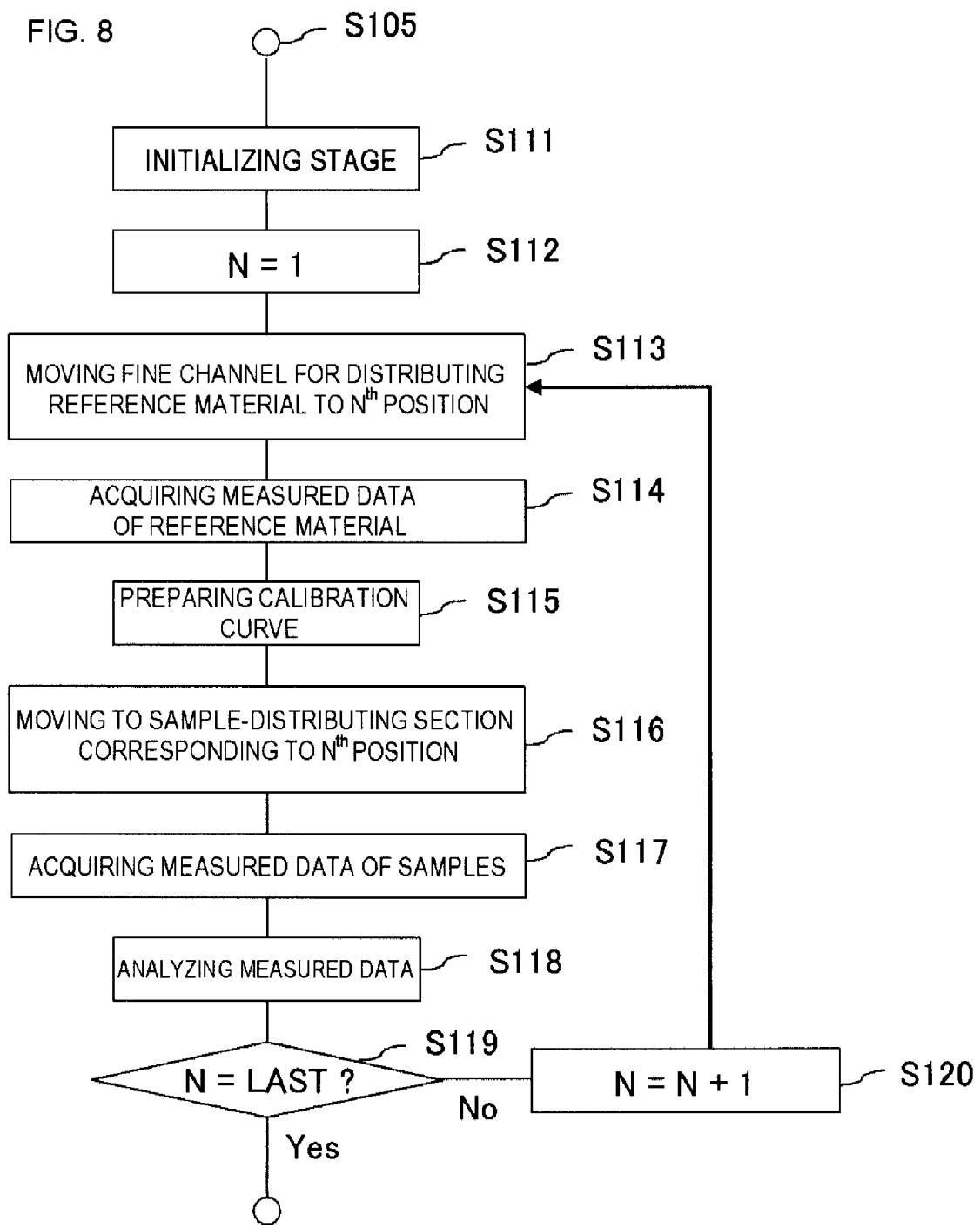
[FIG. 8] It is flow chart of an analysis procedure in an embodiment.

Next, a procedure of the mass spectrometry employing the mass spectrometry system 130 will be described. FIG. 8 is a flow chart of details of the mass spectrometry procedure of step 105 in FIG. 6(a).

Here, for example, in the microchip 100 of several-centimeter square, a presence of an irregularity such as a smaller warpage in the microchip 100 causes a variation in the distance between the microchip 100 and the detector of the mass spectrometer (detecting unit 143 of mass spectrometry system 130), depending upon the position on the substrate 120. Thus, even if the materials of the same mass are concerned, variation is generated in the flight time of ion during the mass measurement, resulting in a variation in the measured values. In order to reduce such variation, measurements of the reference material in the fine channel 102 for distributing the reference material should be conducted by every small region, which is assumed to be on substantially the same surface, to carry out mass calibrations for the mass spectrometry system 130. The mass calibration is, for example, conducted before the measurement of the sample. In this case, a measurement of a sample for mass spectrometry is conducted subsequently to the calibration. For example in the microchip 100 of several-centimeter square, more specifically, it is necessary to repeatedly conducted cycles of the mass calibration and the measurement of the sample in every several-millimeter square.

To solve the problem, in the procedure shown in FIG. 8, first of all, a position of the adaptor 131 disposed on the stage 133 is initialized (S111), and an origin is set. When the samples for mass spectrometry separated in the channel 101 for separation are sequentially scanned, the controller unit 141 refers the coordinate information of the fine channel 102 for distributing the reference material, which is previously defined and stored in the data storage 149, and then the stage 133 is moved along the surface direction to move thereof to a first position (N=1) of the fine channel 102 for distributing the reference material (S112, S113).

The measurement data of the mass spectrometry spectrum for the reference material is acquired in this position (S114). The step 114 includes a step for irradiating a laser beam (FIG. 6(b)) of the above-described step 106.

In addition, in the step 114, detecting unit 143 detects several types of reference materials, mass of which are known. The detected results may be stored in the data storage 149.

Then, the analyzing unit 145 compares the measured value detected by the detecting unit 143 with the theoretical value previously stored in the data storage 149 to conduct the mass calibration. In such case, for example, data of the calibration curve is prepared as calibration data in reference to a formula for presenting a calibration curve stored in the data storage 149 (S115). The prepared data of the calibration curve may be stored in the data storage 149.

Subsequently, the controller unit 141 controls the actuating unit for the stage 133 to move the stage 133, so that a laser beam from the laser source 137 is disposed in a small region of the channel 101 for separation, which corresponds a periphery of the calibration position (first position) on the fine channel 102 for distributing the reference material (S116).

Then, a laser beam is irradiated on the sample for mass spectrometry disposed in such small region, and measurement data of mass spectrometry is acquired by the detecting unit 143 (step 117). The step 117 includes the above-described step for irradiating a laser beam in the step 107 (FIG. 6(b)). When a plurality of samples are disposed in a small region in the channel 101 for separation corresponding to a single calibration position on the fine channel 102 for distributing the reference material, combinations of step of the step 116 and the step 117 are consecutively repeated to acquire the measurement data of the respective samples. The detecting unit 143 may store the acquired measurement data in the data storage 149. The sample-distributing section on the channel 101 for separation corresponding to a single calibration position is positioned away at a distance of, for example, less than several millimeters from the calibration position.

The analyzing unit 145 calibrates the measurement data of the samples in reference to the measurement data of the samples detected by the detecting unit 143 and the data of the calibration curve obtained in the step 115 to provide an analysis (S118). The analyzing unit 145 may transfer the analysis results to the displaying unit 147 to display them on a screen or papers in the displaying unit 147.

Thus, the measurements for the sample-distributing section corresponding to the first position in the fine channel 102 for distributing the reference material is achieved. Subsequently (No in step 119), an actuating unit of the stage 133 moves the stage 133, so that an irradiated position of the laser beam emitted from the laser source 137 coincides with a second position on the fine channel 102 for distributing the reference material (S120). Then, the procedures after the step 113 are repeated for the second position of the fine channel 102 for distributing the reference material. Afterward, the respective procedures after the step 113 are repeated (No in step 119) until the measurements of the samples separated into N pieces in the channel 101 for separation are finished (Yes in step 119).

In addition to above, in the above-described procedures the analysis of the measurement data of samples in the step 118 may be collectively carried out after the measurements of the all samples separated in the channel 101 for separation are finished (Yes in S119).

In addition, when the mass measurements are conducted skipping some parts in the case that it is not necessary to continually scan for the channel 101 for separation, such as in a case that the position of the converging sample in the channel 101 for separation is known, it is sufficient that the measurement data of reference material is acquired by employing the positions that are nearest to the positions of the respective samples for mass spectrometry in the fine channels 102 for distributing the reference material in the step 114 and the mass calibration in the step 115 is conducted by employing the acquired data.

Figure 12:
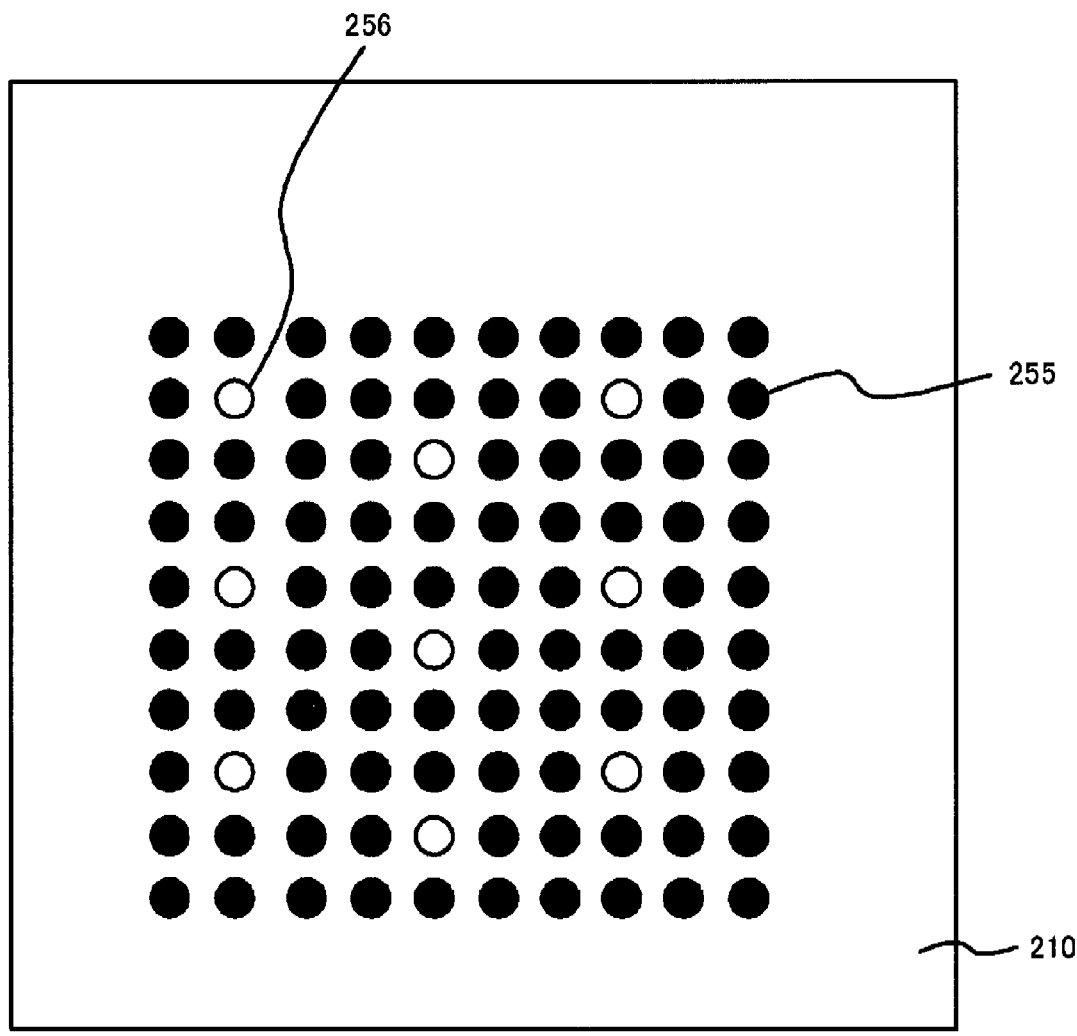
[FIG. 12] It is a plan view, illustrating a configuration of a target plate.

The following advantageous effects can be obtained by employing the microchip 100 as the target board of mass spectrometry. First advantage is that, a single supply of the standard sample to the fine channel 102 for distributing the reference material allows a simple, rapid and sure distribution of a number of reference materials for a number of samples for mass spectrometry in vicinity of the respective samples for mass spectrometry. While the required number of reference materials should be spotted in the conventional target plate as described above in reference to FIG. 12, the microchip 100 is provided with the channel 101 for separation in vicinity of the fine channel 102 for distributing the reference material along the fine channel 102 for distributing the reference material, such that the calibrations can be achieved by employing the fine channel 102 for distributing the reference material for all of the measurements of multiple locations in the channel 101 for separation.

Second advantage is that, since the design is made to provide the separable minimum distance between the fine channel 102 for distributing the reference material and channel 101 for separation, a time for transferring the samples, which is time-consuming in the actual measurements and is required in the alternate measurement, can be minimized. Thus, the total measurement time can be reduced.

Third advantage is that, since the channel 101 for separation is disposed along the fine channel 102 for distributing the reference material, the calibration employing the fine channel 102 for distributing the reference material can be achieved with an improved certainty in the measurement of the constituents located in all regions in the channel 101 for separation. Thus, precision measurements for the mass of each constituent can be achieved.

Fourth advantage is that, since the microchip 100 can be employed as a disposable target board, stable mass spectrums can be acquired by utilizing fresh surface in each time.

As described above, according to the microchip 100, the mass measurements of the samples can be conducted while carrying out the mass calibration by employing the fine channel 102 for distributing the reference material, in the case of directly employing thereof as a target of MALDI-TOF type mass spectrometer. Thus, in the fields that particularly require precise mass measurements such as, for example, researches in biology, drug discovery, diagnosis, health care and the like, the microchip 100 can be extensively utilized as instruments for conducting simple and rapid mass calibrations.

While the descriptions have been made in the above descriptions on the exemplary implementation, in which a position of an irradiation of a laser beam on the microchip 100 is moved by moving the stage 133, the position of the adaptor 131 having the microchip 100 disposed thereon may be fixed when the microchip 100 is employed for a mass spectrometry, and then the controller unit 141 may helps moving the laser source 137 to move a position of an irradiation of a laser beam.

For example, the mass spectrometry system 130 may further include a light source support (not shown) for retaining the laser source 137, and an operation of the stage 133 or the light source retainer may be controlled so that the controller unit 141 helps moving one of the microchip 100 and the light source retainer relative to the other thereof to move the position of the irradiation of a laser beam on the surface of the microchip 100. In addition, in such configuration, the laser source 137 and the light source retainer may be configured so that the surface of the microchip 100 is irradiated with a beam at substantially constant irradiating angle of the beam in the position of the irradiation of the beam. This can provide the configuration, in which a laser beam is further stably irradiated over the microchip 100.

According to the present embodiment, the position of the irradiation of the beam on the microchip 100 can be controlled from the outside of the mass spectrometry chamber 135 to be moved by the shortest move of the stage between the reference material and the samples for mass spectrometry or by the shortest move of laser beam. Thus, the mass calibration of the apparatus with the reference material and the mass measurement of the sample for mass spectrometry can be alternately conducted with a certainty by the respective small regions, in which a warpage or an ununiformity in the thickness of the microchip 100 can be ignored, to achieve the precision measurement of the mass. Thus, precision measurements can be achieved for a plurality of samples for mass spectrometry on the microchip 100.

SECOND EMBODIMENT

While the exemplary implementation having the channel 101 for separation and the fine channel 102 for distributing the reference material, which are parallel straight channels, has been described in first embodiment, planer shapes of the fine channel 102 for distributing the reference material and the channel 101 for separation are not limited to straight lines, and other geometry may also be employed. Such configuration will be described in the present embodiment.

Figure 2:
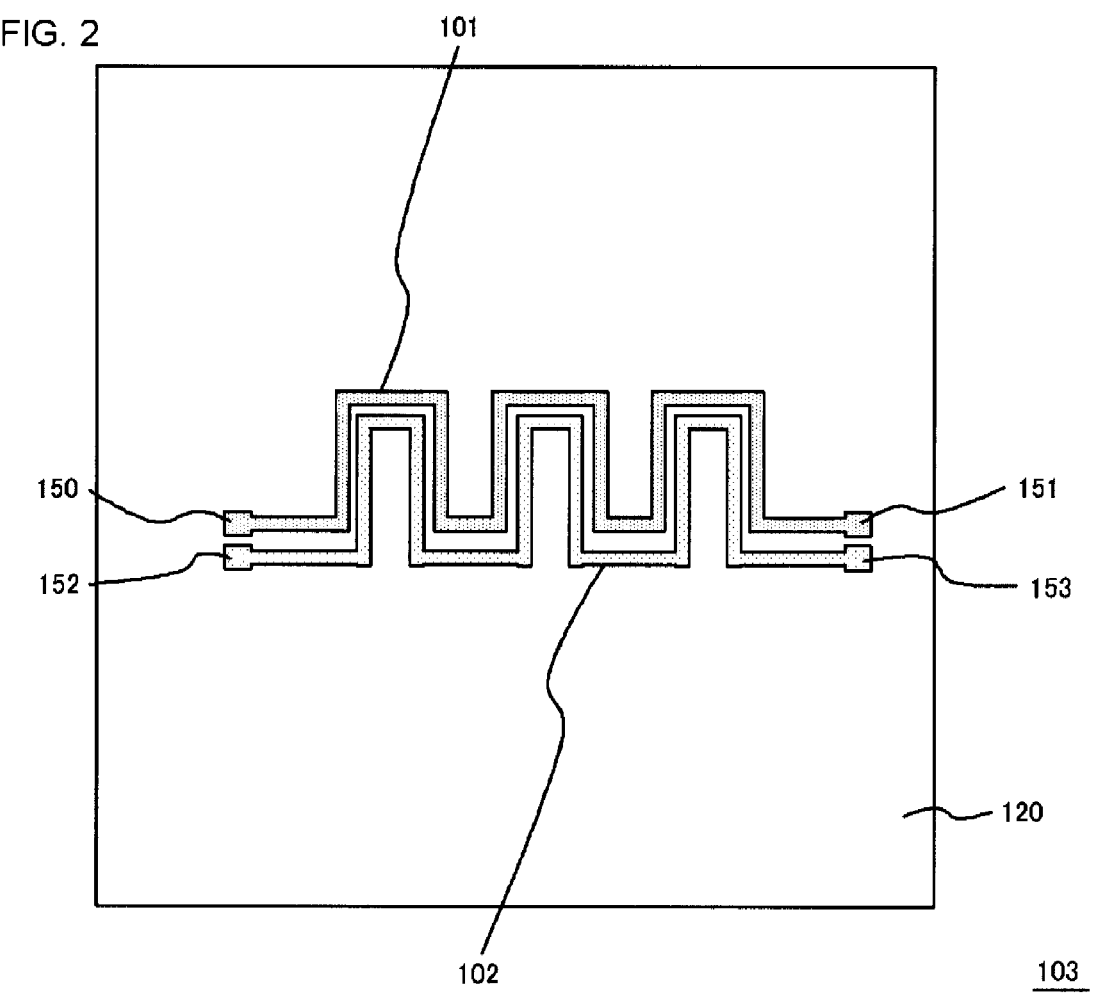
[FIG. 2] It is a plan view, illustrating a configuration of a microchip in an embodiment.

FIG. 2 is a plan view, illustrating a configuration of a microchip of the present embodiment.

While the basic configuration of a microchip 103 shown in FIG. 2 is similar to that of the above-described microchip 100 in reference to FIG. 1 in first embodiment, planer shapes of a channel 101 for separation and a fine channel 102 for distributing the reference material are different therefrom. In the microchip 103, planer shapes of the fine channel 102 for distributing the reference material and the channel 101 for separation are zigzag-shaped, and have corners of about 90 degrees. The fine channel 102 for distributing the reference material is disposed in vicinity of the channel 101 for separation.

The microchip 103 may be used by employing, for example, a method similar to the method for the microchip 100 (FIG. 1) described above in first embodiment.

Since the channel 101 for separation is also provided along the fine channel 102 for distributing the reference material in the lateral side of the fine channel 102 for distributing the reference material in the microchip 103, the advantageous effects same as in first embodiment are obtained. In addition, since the planer shapes of the channel 101 for separation and the fine channel 102 for distributing the reference material are zigzag-shaped in the microchip 103, an increased channel length of the channel 101 for separation, which is longer than a straight channel 101 for separation, can be utilized, when the comparison is made in the condition of the microchips having the same distance along the side in the elongating direction. More specifically, when the substrate 120 is rectangular, the channel length of the channel 101 for separation may be longer than the length of the longer side thereof. Thus, further improved separability for the samples in the channel 101 for separation can be provided.

In addition, even if a number of constituent are contained in the sample, different constituents can be discretely arranged with a certainty, since longer channel length of the channel 101 for separation can be assured in the microchip 103. Thus, the mass spectrometry for the constituents in the sample can be conducted with an improved certainty. In addition, larger number of sample-distributing sections can be provided in a single channel 101 for separation.

While the exemplary implementations, in which curvatures are regularly arranged in the channel 101 for separation and in the fine channel 102 for distributing the reference material and the planer shapes of these channels have zigzag-shapes with corners have been described the present embodiment, it may be sufficient that the channel 101 for separation is provided in the lateral side of the fine channel 102 for distributing the reference material along the fine channel 102 for distributing the reference material, and alternatively, other planer shape may employed. For example, a tip of a corner of the channel may be processed to be rounded. Alternatively, planer shapes of the channel 101 for separation and the fine channel 102 for distributing the reference material may be a geometry having a wave-shape, or a bend such as a U-shape. Alternatively, the planer shape of the channel 101 for separation and with the planer shape of the fine channel 102 for distributing the reference material may be homothetic.

THIRD EMBODIMENT

While the exemplary implementations, in which the constituents in the samples are disposed in plurality of positions in the channel 101 for separation by separating the samples in the channel 101 for separation, is described in the above-described embodiment, the sample-distributing sections are not limited to being provided in the channel. For example, the sample-distributing sections may form a scattered pattern, in which the samples for mass spectrometry are separated and are capable of being spotted.

Figure 3:
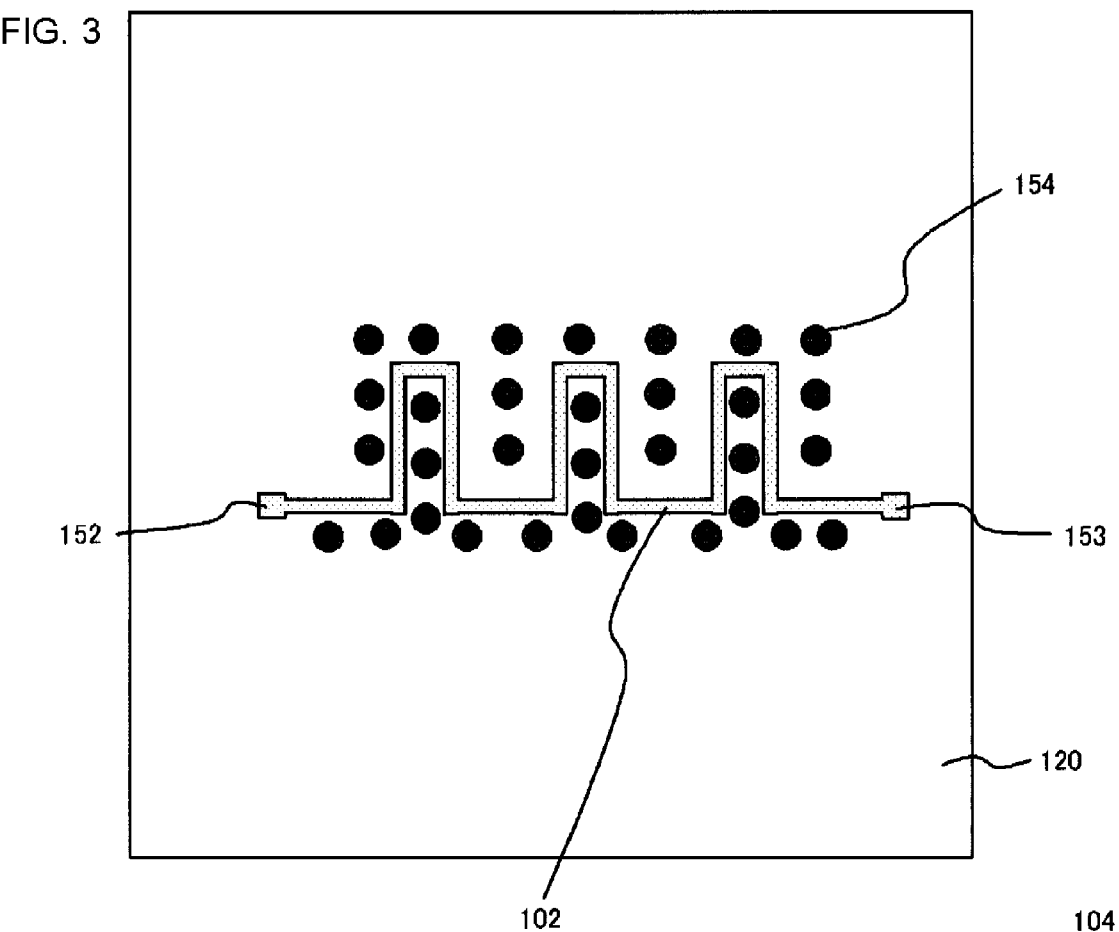
[FIG. 3] It is a plan view, illustrating a configuration of a microchip in an embodiment.

FIG. 3 is a plan view, illustrating a configuration of a microchip of the present embodiment. While the basic configuration of a microchip 104 shown in FIG. 3 is similar to that of the above-described microchip 103 in reference to FIG. 2, the different point is that wells 154 for plurality of sample for mass spectrometry distribution are provided in place of the channel 101 for separation.

In the microchip 104, the fine channel 102 for distributing the reference material is provided in the substrate 120 to form a trench-like geometry, the plurality of sample-distributing sections are a plurality of pores (wells 154 for distributing the samples for mass spectrometry) that are discretely provided in the substrate 120, and the wells 154 for distributing the samples for mass spectrometry is provided in the lateral side of the fine channel 102 for distributing the reference material along the fine channel 102 for distributing the reference material. The wells 154 for distributing the samples for mass spectrometry is two-dimensionally arranged in the surface of the substrate 120, and are disposed along the channel 101 for separation in the vicinity thereof.

Depths of all of the wells 154 for distributing the samples for mass spectrometry may be substantially same as the depth of the fine channel 102 for distributing the reference material. Having such configuration, the calibration in the mass spectrometry can be conducted with further improved certainty.

While the planer shape of the fine channel 102 for distributing the reference material is zigzag-shaped in the microchip 104, it may be sufficient to configure that a plurality of wells 154 for distributing the samples for mass spectrometry are arranged in the side of the fine channel 102 for distributing the reference material, and the planer shape of the fine channel 102 for distributing the reference material is not limited to a zigzag-shape.

Since a plurality of wells 154 for distributing the samples for mass spectrometry are also arranged along the fine channel 102 for distributing the reference material in the microchip 104, advantageous effects similar to that for the above-described embodiments can also be obtained.

In addition, since the fine channel 102 for distributing the reference material, which extends through the vicinity of all the sample for mass spectrometry contained in respective compartments that are separated to have relatively larger dimension, is provided in the substrate 120 that includes the wells 154 for distributing the samples for mass spectrometry, which is capable of having the samples for the mass spectrometry disposed therein to form a spot-pattern in the microchip 104, a shorter distance with the reference material for calibration can be maintained for all the samples for mass spectrometry.

In addition, while the samples for mass spectrometry are necessary to be spotted to the respective wells 154 for distributing the samples for mass spectrometry by an operator or a robot, the reference material can be extended over the entire fine channel 102 for distributing the reference material by merely introducing thereof to one end of the fine channel 102 for distributing the reference material. Thus, the reference material having the same constituent can be arrange at a time in vicinity of all samples for mass spectrometry.

In addition, in the microchip 104, a plurality of wells 154 for distributing the samples for mass spectrometry are provided in the lateral side of the fine channel 102 for distributing the reference material along the fine channel 102 for distributing the reference material. Thus, calibrations for the respective wells 154 for distributing the samples for mass spectrometry can be achieved by using regions that are closer to the fine channel 102 for distributing the reference material. Thus, when the measurements are conducted for a plurality of wells 154 for distributing the samples for mass spectrometry, an improved calibration accuracy can be achieved for each of the pores.

Since the fine channel 102 for distributing the reference material can be stably manufactured in the substrate 120 by employing a microfabrication process in the present embodiment, the microchips having the fine channel 102 for distributing the reference material can be stably manufactured. Further, materials such as silicone resins, silicon or a glass are employed as the material of the substrate 120, so that the fine channel 102 for distributing the reference material can be easily formed via a microfabrication process, as compared with the case of employing materials such as stainless steel, which is conventionally employed for a target plate.

In addition, more wells 154 for distributing the samples for mass spectrometry can be disposed in the lateral side of the fine channel 102 for distributing the reference material by employing the zigzag-shaped planer shape of the fine channel 102 for distributing the reference material. Thus, an increase number of samples that can be measured by employing a single piece of microchip can be achieved. In addition, the respective wells 154 for distributing the samples for mass spectrometry can be arranged with certainty in the lateral side of the fine channel 102 for distributing the reference material by employing the zigzag-shaped planer shape of the fine channel 102 for distributing the reference material, even if the wells 154 for distributing the samples for mass spectrometry are configured to be two-dimensionally arranged in the surface of the substrate.

In addition to above, in the present embodiment, the surface of the fine channel 102 for distributing the reference material may be provided with a bumpy structure, similarly as in first and second embodiments. In addition, the surfaces of the wells 154 for distributing the samples for mass spectrometry may be provided with bumpy structures. For example, a plurality of columnar members may be formed in the wells 154 for distributing the samples for mass spectrometry.

In addition, regions in the surface of the substrate 120 except the region where the fine channel 102 for distributing the reference material and the wells 154 for distributing the samples for mass spectrometry are formed may also be coated with a water repellent material such as Teflon™ by employing the method described above in first embodiment to achieve a water repellent-process in the present embodiment. This can prevent mutual contamination of the samples in the wells 154 for distributing the samples for mass spectrometry and the reference material in the fine channel 102 for distributing the reference material.

While embodiments of the present invention has been fully described above in reference to the annexed figures, it is intended to present these embodiments for the purpose of illustrations of the present invention only, and various modifications other than that described above are also available.

For example, as long as a plurality of sample-distributing sections are arranged along the fine channel 102 for distributing the reference material in vicinity thereof, the geometry thereof is not limited to the configuration described above. In other words, in microchips, in which a warpage of a substrate or a ununiformity in thickness is a problem, the geometry that can be utilized for the calibration of the error may be applicable.

In addition, while the exemplary implementation provided with a single fine channel 102 for distributing the reference material in a single piece of microchip is illustrated in the above embodiments, a plurality of fine channels 102 for distributing the reference material may alternatively be provided in a single piece of microchip. Concerning the microchip including a plurality of fine channels 102 for distributing the reference material, a block may be defined by every single fine channel 102 for distributing the reference material or a block may be defined by several fine channels 102 for distributing the reference material, and a plurality of sample-distributing sections may also be provided in vicinity thereof.

In addition, while the configuration, in which a single channel 101 for separation is provided in a single piece of microchip, is exemplified in first and second embodiments, a plurality of channels 101 for separation may alternatively be provided in a single piece of microchip. Concerning the microchip including a plurality of channels 101 for separation, the respective channels 101 for separation are arranged along the fine channel 102 for distributing the reference material in the lateral side thereof, so that easier calibration can be achieved, providing precise mass spectrometry. In addition, in such case, according to the length of the channel 101 for separation, a calibration for a block may be conducted by each channel 101 for separation, or a calibration may alternatively be conducted for a predetermined one block including a plurality of channel 101 for separation.

EXAMPLE

In the following description, a specific example will be described in reference to the microchip 100 of first embodiment.

In the present example, an isoelectric focusing and mass spectrometry for peptide samples are conducted by employing the microchip 100 shown in FIG. 1.

Quartz glass is employed for a material of the substrate 120. Two straight parallel fine channels are manufactured on the substrate 120 by an exposure to light. Then, an ashing of the surface of the substrate 120 is conducted with ozone, and thereafter, "polyolefin micro sealing tape 9795", commercially available from 3M, is applied on the channel 101 for separation and on the fine channel 102 for distributing the reference material to be employed as a cover.

Isoelectric focusing of the samples is conducted by employing the obtained microchip 100. A peptide mixture is employed for a sample for mass spectrometry supplied in the channel 101 for separation. In the isoelectric focusing, a sample obtained by mixing a commercially available peptide and a carrier ampholite is supplied from a liquid receiver 150 or a liquid receiver 151, which are communicated with the channel 101 for separation. After the supply, the sample is left for several minutes, and then the sample reaches the liquid receiver of the opposite side via a capillary phenomenon.

Next, the liquid receiver in the positive side is fulfilled with phosphoric acid aqueous solution and the liquid receiver in the negative side is fulfilled with sodium hydroxide. Electrodes (not shown) are disposed in the liquid receiver 150 and in the liquid receiver 151, and a DC voltage is applied between the electrodes. More specifically, a DC voltage of 900 V is applied between the liquid receivers in the both ends for the channel having the length of about 15 mm.

Shortly subsequent to applying a voltage for an isoelectric focusing, a reference material solution containing a plurality of commercially available calibration samples for mass spectrometry dissolved therein is supplied to the liquid receiver 152 or the liquid receiver 153, both of which are in communication with the fine channel 102 for distributing the reference material. In such case, a vacuum tweezers is employed for a drawing operation, so that the entire fine channel 102 for distributing the reference material is fulfilled with the reference material solution in several seconds. As described above, in the microchip 100, the reference material is simply and rapidly arranged. In addition to above, the fine channel 102 for distributing the reference material is not energized, and is left without changing the condition.

The isoelectric focusing is completed about 2 minutes after starting the energization to the channel 101 for separation. Converged peptide bands of the same number as the number of types of the samples for mass spectrometry peptide are formed in the channel 101 for separation. The respective regions for forming the respective peptide bands are the sample-distributing sections. In such case, the fine channel 102 for distributing the reference material is already fulfilled with the reference material.

Thereafter, the microchip 100 is transferred onto the horizontal metal mount (not shown) cooled with liquid nitrogen to freeze liquids in the channel 101 for separation and in the fine channel 102 for distributing the reference material. The seal utilized as a cover is naturally removed after being left for a certain period. The frozen sample is freeze-dried to eliminate water to fix the peptide sample in a form of a solid-like state to the channel 101 for separation. In such case, the reference material in the fine channel 102 for distributing the reference material is also dried.

Meanwhile, a saturated solution of $\alpha$-cyano-4-hydroxycinnamic acid ($\alpha$-CHCA) is prepared in advance for a matrix. Such matrix solution is sprayed over the entire surface of the microchip 100, which is in a condition after the freeze-drying process. When an atomizer, for example, is employed, the matrix solution is adhered onto the surface of the microchip 100 in a form of fine particles having diameter of equal to or smaller than 500 µm. These are adhered onto dehydrated peptide remaining in the channel 101 for separation of microchip 100 and dehydrated reference material fulfilled in the sample powder-fine channel 102 for distributing the reference material, causing the powder being dissolved into drop of the matrix. In such case, if the peripheral temperature is controlled to dry these materials in several seconds, the respective samples or the reference material, which have been once mixed with the matrix, is through the process for drying to form mixed crystal.

In addition to above, a solution of the reference material mixed with the matrix may be previously prepared, and may be supplied to the fine channel 102 for distributing the reference material. In such case, the solution is dried after the freeze drying to form mixed crystal.

The microchip 100 thus prepared is directly utilized as a target board of MALDI-TOF mass spectrometer. An adaptor having an outer shape, which is similar to that of a standard target of a mass spectrometer, is prepared, and the microchip 100 is mounted onto such adaptor to conduct the measurements. The adapter is installed on an XY-stage, which is controllable by a computer, and thus is positionally controlled with a controller computer.

Since a distance between the microchip 100 and the detecting element of the mass spectrometer are not constant by locations in the microchip 100 of several centimeter square caused by the smaller warpage of the microchip 100, variations are generated in the measured values during the mass measurements even if the same mass material are measured. In order to correct such variation, it is necessary to conduct the measurements while conducting a mass calibration by ranges that can be considered as substantially the same surface. In reality, it is necessary to conduct measurements of samples while repeating the mass calibration by several millimeter square.

Figure 9:
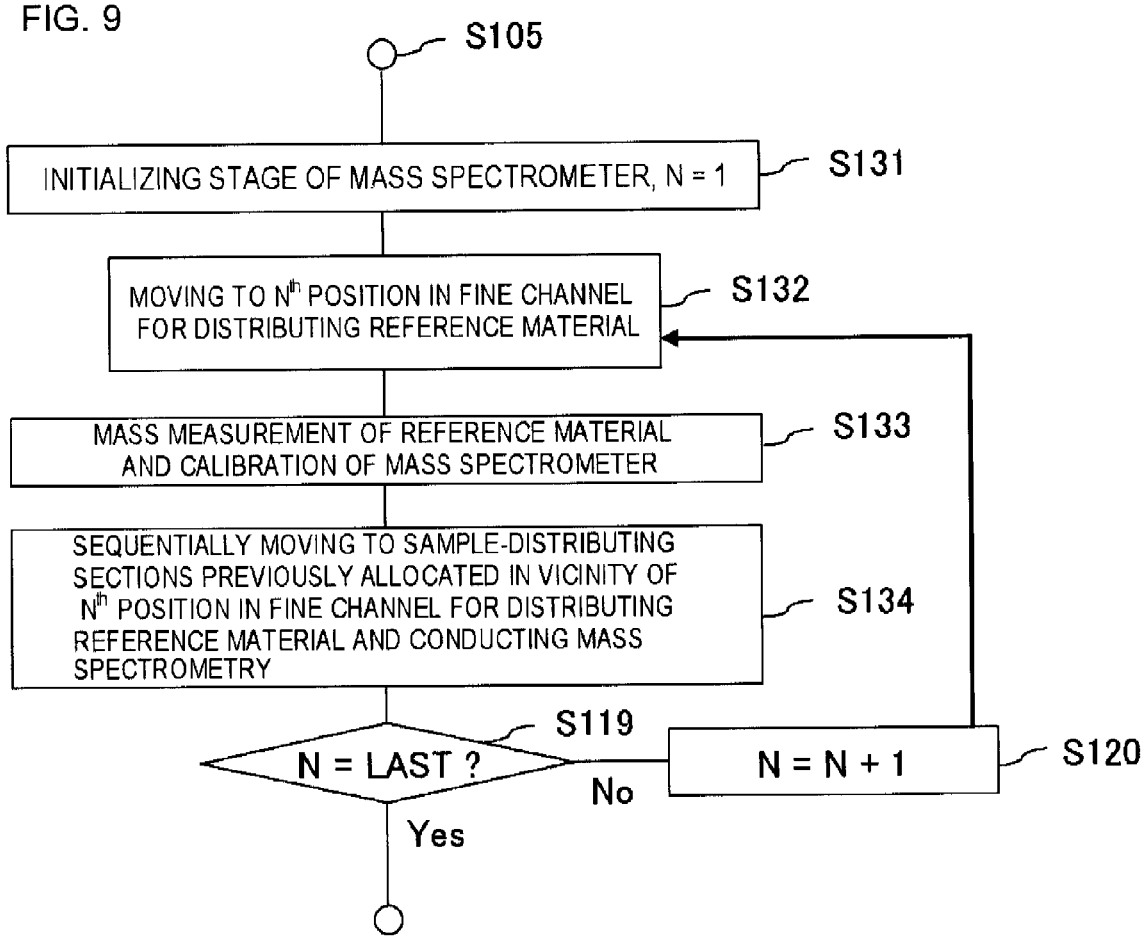
[FIG. 9] It is flow chart of an analysis procedure in an example.
Figure 10:
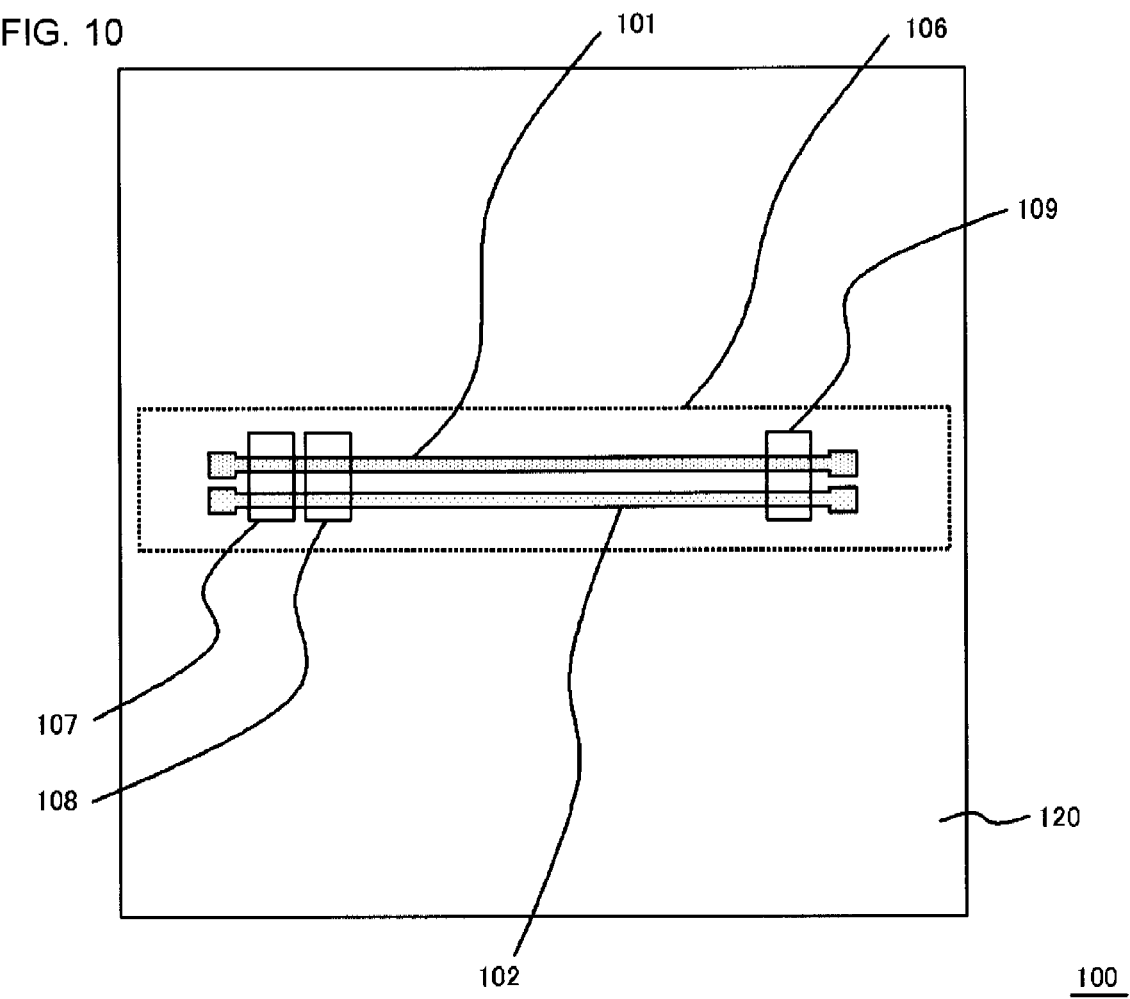
[FIG. 10] It is a diagram, describing a compartment and a small region of the microchip in an embodiment.
Figure 11:
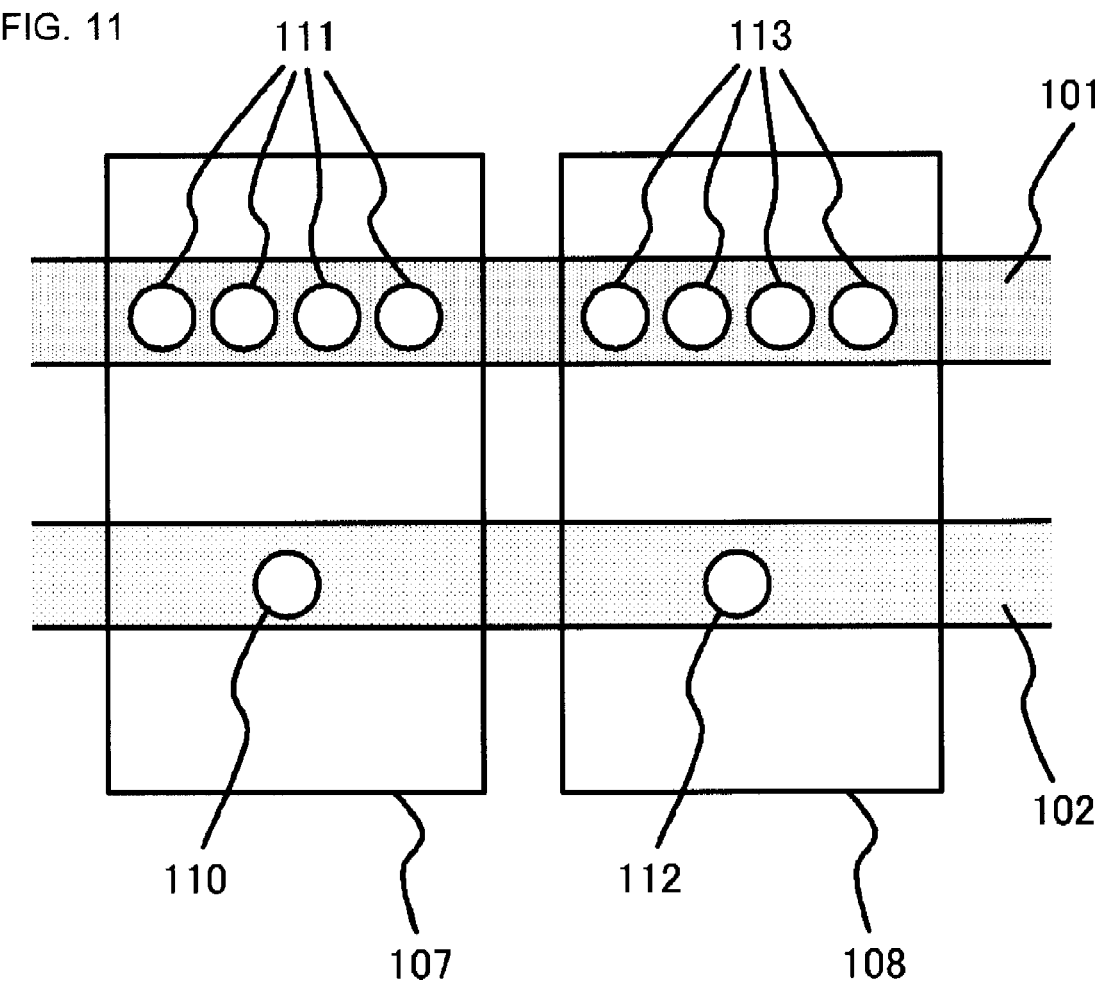
[FIG. 11] It is an enlarged view of the small region in FIG. 10.

FIG. 9 is a flow chart of an analysis procedure in the present example. FIG. 10 is a diagram of describing blocks and small regions in mass spectrometry for the microchip 100. FIG. 11 is an enlarged view of a small region in FIG. 10. Description will be made in reference to the following figures.

In the beginning, the microchip 100, in which mixed crystal with the matrix is previously prepared by employing the method described above, is installed to an adaptor, which has a geometry same as the standard target of the employed mass spectrometer. More specifically, a recess, which is capable of installing the microchip therein in the center of the adaptor, is manufactured, and the microchip is fixed by a holding member that can prevent dropping thereof. This adapter is mounted to the mass spectrometer. A program for automatically executing the steps illustrated in the following description may be previously installed in the controller personal computer (PC) for the mass spectrometer, and the program may be automatically executed, or may be manually executed step by step.

Then, a position of the adaptor having the microchip 100 mounted therein is initialized (S131 of FIG. 9). For such reference point, previously defined coordinate on the microchip 100 is utilized to conduct a mass calibration and a mass measurement.

First of all, the stage is moved to a position (indicated by 110 in FIG. 11) defined as a position 1 in the fine channel 102 for distributing the reference material (S132 in FIG. 9). Then, a mass spectrum of the reference material is acquired. Values of mass to charge ratio (m/z) that correspond to peaks are compared with a mass to charge ratio (m/z) previously stored in a controller PC to achieve a calibration of the mass spectrometer (S133 of FIG. 9).

Next, the mass measurements are sequentially conducted for respective sample-distributing sections in the channel 101 for separation disposed in the small regions 107 including the position 1, which have been defined as regions to be considered as substantially same planes as that also includes the position 1 (S134 of FIG. 9). FIG. 11 illustrates the example provided with four sample-distributing sections 111 corresponding to the position 1 in the channel 101 for separation.

When all the measurements for the sample-distributing sections 111 are completed, the stage is moved to a position in the fine channel 102 for distributing the reference material, which has been defined as a position 2 (indicated by 112 in FIG. 11) (No of S119, S120 and S132 of FIG. 9), the mass spectrum of the reference material is acquired, and the calibration of the mass spectrometer is conducted, similarly as in the case for the position 1 (S133 of FIG. 9).

Then, the mass measurements are sequentially conducted for respective sample-distributing sections in the channel 102 for separation disposed in the small regions 108 including the position 2, which have been defined as regions to be considered as substantially same planes as that also includes the position 2 (S134 of FIG. 9).

Afterward, the mass calibration and the mass measurement are repeated until reaching the previously defined last position, or in other words the small region 109 including the position N (Yes of S119 of FIG. 9), and when the last mass measurement is finished, all the measurements are finished for a block 106 in measurement.

While a combination of the channel 101 for separation and the fine channel 102 for distributing the reference material is defined as one block 106 in the measurement in the microchip 100, when a plurality of channels 101 for separation is included, it is sufficient that the respective channels 101 for separation may be defined as one block in the measurement, and the measurements for the respective blocks may be carried out in the procedure described above.

A specific example will be shown in the following description.

"MS-CAL2" commercially available from Sigma-Aldrich Corporation is employed as a reference material. Five types of equimolar peptides contained in such "MS-CAL2" are mixed, and the obtained peptide mixture is utilized as a sample for mass spectrometry. Monoisotopic mass of the five types of peptides are: 757.3997; 1046.5423; 1533.8582; 2465.1989; and 3494.6513. In addition, α-CHCA is employed as a matrix. The reference material and the matrix are mixed to prepare the reference material liquid mixture. A separating channel of the microchip and the fine channel for the reference material distribution are filled with the reference material liquid mixture to prepare a target board of the MALDI-TOF mass spectrometer.

"AXIMACFR Plus" commercially available from Shimadzu Corporation is employed for the mass spectrometer, and the target board made on the adaptor is installed to conduct the measurement of the peptide mixture. First of all, while a mass error of from 6 to 25 is detected depending on the position of the separation channel when the measurement is conducted without mass calibration, no specific tendency in the distribution of the mass error by locations is found. Thus, it can be understood that no precise mass measurement is achieved without a mass calibration. Next, the measurement of the peptide mixture is carried out while conducting five points of calibration with the reference material. Then, the mass error is reduced to from 0 to 1 in the entire channel.

From the above-described results, it is shown that the mass calibrations are conducted in dual meanings. More specifically, one is a mass calibration of the chip itself, and the other is a mass calibration within the chip. The mass calibration of the chip itself allows a comparison with the data measured by the different chip. In addition, the distribution of the mass error, which has been present along the channel in condition without a calibration, is corrected by the mass calibration within the chip, and therefore the same measurement result can be obtained even if the measurement is conducted in any position on the same channel. Therefore, the present microchip allows conducting the mass calibration by a simple method.

The invention claimed is:

1. A microchip, capable of being employed as a target board of a mass spectrometry, comprising:
    a substrate;
    a plurality of sample-distributing sections, provided in said substrate and containing a sample for mass spectrometry distributed therein; and
    a reference material-supplying channel, provided in said substrate and being supplied with the reference material for said mass spectrometry,
    wherein said plurality of sample-distributing sections are provided in the lateral side of said reference material-supplying channel along said reference material-supplying channel.

2. The microchip as set forth in claim 1,
    wherein said plurality of sample-distributing sections are provided in the sample-distributing channel provided in said substrate,
    wherein said sample-distributing channel is provided along said reference material-supplying channel,
    wherein said reference material-supplying channel and said sample-distributing channel are provided in said substrate to form trench-like arrangement, and
    wherein constituents in said sample are separated in said sample-distributing channel.

3. The microchip as set forth in claim 2, wherein said sample-distributing channel includes an isoelectric focusing region, in which a pH gradient is generated, and further comprising:
    a pair of electrode that applies an electric field to said isoelectric focusing region; and
    a sample-supplying unit that supplies said sample into said isoelectric focusing region.

4. The microchip as set forth in claim 2, wherein said sample-distributing channel is disposed along a direction of an elongation of said reference material-supplying channel in substantially parallel therewith.

5. The microchip as set forth in claim 2, wherein planer shapes of said reference material-supplying channel and said sample-distributing channel are zigzag-shaped.

6. The microchip as set forth in claim 1,
    wherein said reference material-supplying channel is provided in said substrate to form a trench-shape,
    wherein said plurality of sample-distributing sections are a plurality of pores discretely provided in said substrate, and
    wherein said plurality of pores are provided in a lateral side of said reference material supplying channel along said reference material-supplying channel.

7. The microchip as set forth in claim 6, wherein a planer shape of said reference material-supplying channel is zigzag-shaped.

8. The microchip as set forth in claim 1, wherein a distance between said sample-distributing section and said reference material-supplying channel in the substrate surface is equal to or larger than 0.5 mm and equal to or smaller than 10 mm.

9. The microchip as set forth in claim 1, wherein a material of said substrate is silicone resin, silicon or glass.

10. The microchip as set forth in claim 1, wherein a plurality of columnar member are provided in said reference material-supplying channel.

11. The microchip as set forth in claim 1, wherein a hydrophilic treatment is conducted for a surface of said reference material-supplying channel.

12. The microchip as set forth in claim 1, wherein, in a surface for forming said reference material-supplying channel in said substrate, a water repellent treatment is conducted for at least a vicinity of a region for forming said reference material-supplying channel.

13. A mass spectrometry system, comprising:
    a microchip as set forth in claim 1;
    an optical irradiation unit, which is capable of irradiating a laser beam over a predetermined region of said reference material-supplying channel and is capable of irradiating a laser beam over said sample-distributing section near said predetermined region among said plurality of sample-distributing sections;
    a data acquisition unit, which is capable of analyzing ion of said reference material created by the irradiation over said reference material-supplying channel to acquire a mass spectrometry data of said reference material and is also capable of analyzing ion of said sample created by the irradiation over said sample-distributing section near said predetermined region to acquire a mass spectrometry data of said sample; and
    an analyzing unit, which is capable of acquiring calibration data for mass spectrometry of said sample based on the mass spectrometry data of said reference material to analyze mass spectrometry data of said sample based on said calibration data.

14. The mass spectrometry system as set forth in claim 13, wherein a distance between said sample-distributing section and said reference material-supplying channel in the surface of the substrate is larger than a spot diameter of said laser beam.

15. A method of employing the microchip as set forth in claim 1 as a target board of mass spectrometry, comprising:
disposing a sample in said sample-distributing section, said sample serving as a target of a mass spectrometry;
supplying a reference material for said mass spectrometry in said reference material supplying channel; and
conducting a laser desorption/ionization (LDI) time of flight mass spectrometry (TOFMS) of said sample,
wherein said conducting the LDI-TOFMS includes:
irradiating a laser beam over a predetermined region of said reference material-supplying channel; and
irradiating a laser beam over the sample-distributing section located near said predetermined region among said plurality of sample-distributing sections.

* * * * *